US009463072B2

(12) United States Patent
Comaniciu et al.

(10) Patent No.: US 9,463,072 B2
(45) Date of Patent: Oct. 11, 2016

(54) SYSTEM AND METHOD FOR PATIENT SPECIFIC PLANNING AND GUIDANCE OF ELECTROPHYSIOLOGY INTERVENTIONS

(71) Applicants: Dorin Comaniciu, Princeton Junction, NJ (US); Bogdan Georgescu, Plainsboro, NJ (US); Ali Kamen, Skillman, NJ (US); Tommaso Mansi, Plainsboro, NJ (US); Tiziano Passerini, Plainsboro, NJ (US); Saikiran Rapaka, Ewing, NJ (US)

(72) Inventors: Dorin Comaniciu, Princeton Junction, NJ (US); Bogdan Georgescu, Plainsboro, NJ (US); Ali Kamen, Skillman, NJ (US); Tommaso Mansi, Plainsboro, NJ (US); Tiziano Passerini, Plainsboro, NJ (US); Saikiran Rapaka, Ewing, NJ (US)

(73) Assignee: Siemens Aktiengesellschaft, München (DE)

( * ) Notice: Subject to any disclaimer, the term of this patent is extended or adjusted under 35 U.S.C. 154(b) by 193 days.

(21) Appl. No.: 14/455,803

(22) Filed: Aug. 8, 2014

(65) Prior Publication Data
US 2015/0042646 A1 Feb. 12, 2015

Related U.S. Application Data

(60) Provisional application No. 61/864,205, filed on Aug. 9, 2013.

(51) Int. Cl.
*A61B 5/0402* (2006.01)
*G06T 17/20* (2006.01)
(Continued)

(52) U.S. Cl.
CPC ........... *A61B 19/50* (2013.01); *A61B 5/04028* (2013.01); *A61B 5/7278* (2013.01);
(Continued)

(58) Field of Classification Search
CPC .............. A61B 2018/00839; A61B 5/6885; A61B 2034/742; A61B 2034/105; A61B 2034/107; A61B 2090/364; A61B 34/10; A61B 6/503; A61B 5/055; A61B 5/7425; A61B 5/7475; A61B 6/5247; A61B 2017/00199; A61B 2090/367; A61B 5/0402; A61B 5/0452; A61B 8/0883; A61B 8/4416; A61B 8/483; A61B 2017/00243; A61B 2017/0237; A61B 2018/00351; G06T 2207/10072; G06T 2207/30048; G06T 19/20; G06T 2207/20081; G06T 15/08; G06T 2207/30101; G06T 2210/41; G06T 2207/10136; A61N 1/362; G06F 19/3437; G06K 2209/057
See application file for complete search history.

(56) References Cited

U.S. PATENT DOCUMENTS 4,639,223 A *  1/1987  Keller, Jr. .............. G09B 23/28
                                                      434/272
7,668,354 B2    2/2010  O'Donnell et al.
(Continued)

OTHER PUBLICATIONS

Peyrat et al., "A Computational Framework for the Statistical Analysis of Cardiac Diffusion Tensors: Application to a Small Database of Canine Hearts,", IEEE TMI, 26(11): 1500-1514, 2007.

*Primary Examiner* — Haixia Du

(57) ABSTRACT

A method and system for patient-specific planning and guidance of electrophysiological interventions is disclosed. A patient-specific anatomical heart model is generated from cardiac image data of a patient. A patient-specific cardiac electrophysiology model is generated based on the patient-specific anatomical heart model and patient-specific electrophysiology measurements. Virtual electrophysiological interventions are performed using the patient-specific cardiac electrophysiology model. A simulated electrocardiogram (ECG) signal is calculated in response to each virtual electrophysiological intervention.

50 Claims, 14 Drawing Sheets

(51) Int. Cl.
*G06T 7/00* (2006.01)
*A61B 5/00* (2006.01)
*A61B 6/00* (2006.01)
*G06F 19/00* (2011.01)
*A61B 34/10* (2016.01)
*A61N 1/362* (2006.01)
*A61B 19/00* (2006.01)

(52) U.S. Cl.
CPC .............. *A61B 5/743* (2013.01); *A61B 6/486* (2013.01); *A61B 6/503* (2013.01); *A61B 6/5247* (2013.01); *A61B 34/10* (2016.02); *G06F 19/321* (2013.01); *G06F19/3437* (2013.01); *G06T 7/0083* (2013.01); *G06T 17/20* (2013.01); *A61B 6/4441* (2013.01); *A61B 2034/101* (2016.02); *A61B 2034/105* (2016.02); *A61B 2576/023* (2013.01); *A61N 1/3627* (2013.01); *G06T 2200/08* (2013.01); *G06T 2207/30048* (2013.01)

(56) References Cited

U.S. PATENT DOCUMENTS

| | | |
|---|---|---|
| 7,916,919 B2 | 3/2011 | Zheng et al. |
| 2008/0009758 A1* | 1/2008 | Voth ................. A61B 5/042 600/523 |
| 2010/0040272 A1 | 2/2010 | Zheng et al. |
| 2012/0022843 A1 | 1/2012 | Ionasec et al. |
| 2013/0216110 A1 | 8/2013 | Zheng et al. |
| 2013/0226542 A1 | 8/2013 | Rapaka et al. |
| 2014/0022250 A1* | 1/2014 | Mansi ................. A61B 19/50 345/420 |
| 2014/0088943 A1 | 3/2014 | Trayanova et al. |
| 2014/0122048 A1 | 5/2014 | Vadakkumpadan et al. |

* cited by examiner

SYSTEM AND METHOD FOR PATIENT SPECIFIC PLANNING AND GUIDANCE OF ELECTROPHYSIOLOGY INTERVENTIONS

This application claims the benefit of U.S. Provisional Application No. 61/864,205, filed Aug. 9, 2013, the disclosure of which is herein incorporated by reference in its entirety.

BACKGROUND OF THE INVENTION

The present invention relates to planning and guidance of electrophysiology interventions, and more particularly to personalized and interactive planning of electrophysiology interventions using a fast and personalized computational model of the cardiac electrophysiology along with a model of electrocardiogram (ECG) signal generation.

Sudden cardiac death (SCD) is responsible for over 300,000 deaths per year in the United States. Severe cardiac arrhythmias, such as ventricular tachycardia (VT) or ventricular fibrillation (VF), are the most common causes of SCD. Currently, implantable cardioverter-defibrillator devices (ICD) are the primary treatment of choice for patients at high risk for VT or VF. These devices prevent life-threatening VT/VF events by automatically sending strong defibrillator shocks when VT/VF is detected. However, the morbidity associated with ICD shocks is high and ICDs do not provide complete protection against SCD. When arrhythmias become incessant or too severe, an alternative therapy becomes necessary.

Ablation procedures for cardiac arrhythmias have proven to be successful for a large variety of cardiac electrophysiology troubles. Atrial fibrillation (Afib), VT, or VF, for example, can be treated, or at least controlled, in several classes of patients. The general idea behind ablation therapy is to destroy the cells that trigger the arrhythmias. These cells can be ectopic, i.e., they trigger uncontrolled electrical signals spontaneously, or exits points of slow conducting pathways that can be found, for example, around or within myocardium scars. The success of the ablation therapy relies on the ability of the electrophysiologist to identify the arrhythmogenic regions. While Afib ablation has become systematic in most patients, finding the regions to ablate in post myocardium infarction (MI) patients is extremely challenging due to the variability in scar geometry and local tissue substrate. Current practice is still lacking of a systematic clinical strategy, which may explain the rather unsatisfactory success rate of ablation therapies for VT (from 50% to 90%).

Congestive Heart Failure (CHF) is a dramatically widespread disease, affecting more than 23 million people worldwide, and more than 5.8 million in the United States. CHF symptoms are various and affect the patients to different degrees. The New York Heart Association (NYHA) proposed a classification of patients in four groups, from minimally or mildly symptomatic (Class I and II) to moderately or severely symptomatic (Class III and IV). Patients with heart failure often present dyssynchronous ventricular contraction. Cardiac Resynchronization Therapy (CRT) is used to treat this condition by artificially pacing the cardiac muscle through a pulse generator (pacemaker) and multiple leads, including a left ventricle (LV) lead, a right ventricle (RV) lead, and a right atrial (RA) lead. In combination with optimal medical therapy (with or without a defibrillator), CRT has been proven to reduce the risk for hospitalization of CHF patients, and to improve the heart conditions in NYHA Class I and II patients. A recent study showed that the combined use of CRT and an implantable cardioverter defibrillator (ICD) has significant success in the treatment of patients with left bundle branch block (LBBB), a cardiac conduction anomaly detectable with ECG. However, 30% of patients do not respond to the therapy although they are within the guidelines.

One challenge facing the delivery of effective CRT is the left ventricular lead placement. The coronary venous anatomy often limits access to the target pacing area. In addition, the presence of localized scar tissue in the region of the LV lead tip may alter the response to the treatment. Acute haemodynamic studies demonstrate that the increase in the patient's heart conditions is less robust when the LV is paced in an area near a scar. Furthermore, localized LV dyssynchrony, which is common in heart failure patients and detectable by ECG, has a significant impact on overall CRT effectiveness. The interaction between the region of maximal dyssynchrony and the presence of scar tissue adjacent to the LV lead tip has important implications for determining optimal pacing sites. Accordingly, a predictive framework is desirable to select responders and optimize lead configuration for CRT.

In view of the foregoing, there is a need for efficient tools for improving electrophysiology interventions, such as CRT and ablation procedures, in terms of maximizing outcomes, decreasing risks and minimizing intervention time.

BRIEF SUMMARY OF THE INVENTION

The present invention provides a method and system for interactive patient-specific planning and guidance of cardiac electrophysiology (EP) interventions. Embodiments of the present invention provide a comprehensive and interactive method for prediction of cardiac electrocardiograms after EP therapies. Embodiments of the present invention utilize advanced machine learning algorithms, a LBM-EP (Lattice-Boltzmann Method for Electrophysiology) technique for near real-time modeling of cardiac electrophysiology, and a model of generation of ECG signals to predict and display patient-specific electrocardiograms after virtual EP therapies. Embodiments of the present invention provide both pre-operative and intra-operative intervention planning.

In one embodiment of the present invention, a patient-specific anatomical heart model is generated from cardiac image data of a patient. A patient-specific cardiac electrophysiology model is generated based on the patient-specific anatomical heart model and patient-specific electrophysiology measurements. A virtual electrophysiological intervention is performed using the patient-specific cardiac electrophysiology model. A simulated electrocardiogram (ECG) signal is calculated in response to the virtual electrophysiological intervention.

These and other advantages of the invention will be apparent to those of ordinary skill in the art by reference to the following detailed description and the accompanying drawings.

DETAILED DESCRIPTION

The present invention relates to patient-specific planning and guidance of electrophysiology interventions using medical imaging data. Embodiments of the present invention are described herein to give a visual understanding of the methods for patient-specific modeling and electrophysiology simulation using medical imaging data. A digital image is often composed of digital representations of one or more objects (or shapes). The digital representation of an object is often described herein in terms of identifying and manipulating the objects. Such manipulations are virtual manipulations accomplished in the memory or other circuitry/hardware of a computer system. Accordingly, is to be understood that embodiments of the present invention may be performed within a computer system using data stored within the computer system.

Electrocardiography (ECG) is often utilized to assess arrhythmias, conduction abnormalities, and the effects of treatments on the electrical activity of the heart. QRS interval duration, as well as QRS morphology, are strong predictors of good response to CRT therapy. Rhythm assessment after ablation is a necessary step of the patient follow-up, to evaluate the success of the procedure and exclude complication such as asymptomatic atrial fibrillation. With the development of non-invasive treatments, more detailed and predictive electrophysiology (EP) assessment is desirable.

Embodiments of the present invention provide a system and method for personalized and interactive (preoperative or intraoperative) planning of electrophysiology interventions for heart rhythm diseases and heart failure. Embodiments of the present invention utilize a fast computational model of cardiac electrophysiology along with a model of the ECG signal generation. These models reflect actual patient conditions based on preoperative patient data. Embodiments of the present invention provide an automatic, real-time personalization method for use with intraoperative measurements, if available. Embodiments of the present invention simulate virtual electrophysiological interventions and provide interactive evaluation the virtual electrophysiological interventions based on the computation and visualization of ECG-based clinical parameters. In addition, embodiments of the present invention enable real-time updates of the derived clinical parameters by feeding the electrophysiological model with intraoperative data, if available.

Figure 1:
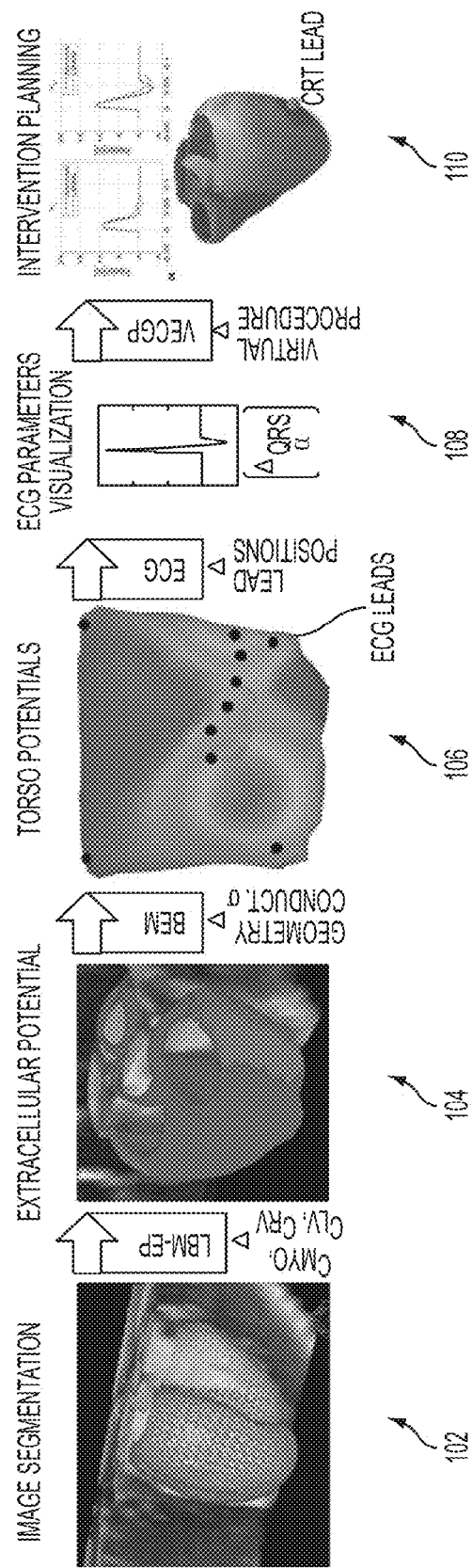
FIG. 1 illustrates an overview of a method for patient-specific planning of electrophysiology interventions according to an embodiment of the present invention.

FIG. 1 illustrates an overview of a method for patient-specific planning of electrophysiology interventions according to an embodiment of the present invention. As illustrated in FIG. 1, preoperative images of the heart (e.g. CT, US, DynaCT, MRI) are segmented to generate a patient-specific anatomical heart model (102). The patient-specific anatomical heart model provides a computational domain for solving a patient-specific electrophysiology model using the Lattice-Boltzmann method for electrophysiology (LBM-EP). If electrophysiological data are available (endocardial mapping, ECG leads, etc. under sinus rhythm or manual pacing), an inverse problem algorithm automatically estimates and updates real-time myocardium diffusion and action potential duration (APD) maps. The system then computes the ECG signals resulting from the calculated EP. In particular, extra-cellular potentials are estimated from trans-membrane potentials calculated by the patient-specific EP model (104), and then trans-membrane potentials are projected onto the torso using a boundary element method (BEM) and ECG leads are derived (106). The torso geometry can be automatically segmented from the images using machine learning algorithms. When the full torso is not available, the heart can be registered to an atlas using Procrustes analysis. An ECG is calculated from the torso potentials at the ECG leads positions and ECG parameters are visualized (108). Intervention planning is performed by simulating intraoperative scenarios by performing virtual interventions and using the advanced ECG-based measurements estimated by the system. If the available imaging data allows the morphological reconstruction of the coronary sinus and the identification of scar tissue, this information is used to guide the lead placement during virtual electrophysiological intervention. For instance, the optimal lead placement for CRT can be assessed interactively, by monitoring improvements in ECG after the virtual intervention. This procedure has the potential advantage of allowing the identification of locations for lead placement that are both effective and feasible, based on the anatomy of the coronary venous system and the presence of localized scar.

Since the system is generative, cardiac electrophysiology can be computed under different virtual interventions. As a result, several therapeutic scenarios can be tested in-silico. If the available images allow the morphological reconstruction of the coronary sinus, as well as the identification of any scar tissue, this information can be used to select feasible sites of intervention. Combining the advance ECG-based measurements estimated by the system and the in-silico interactive system for intervention planning can potentially guide electrophysiologists towards the optimal intervention strategy while minimizing life-threatening risks for the patient. According to an advantageous aspect of the present invention, the fast patient-specific electrophysiology modeling allows evaluation of electrophysiological interventions to be achieved in-silico by virtual generation of ECG signals, which are displayed by the system. ECG-based measurements provide clinically relevant indicators of the success of the procedures. According to another advantageous aspect, the outcome of several different virtual interventions, performed interactively with the system by placing leads or ablate regions of the myocardium tissue, can be quantitatively compared before implementing them. According to another advantageous aspect, if available medical images allow for the reconstruction of the morphology of the coronary sinus, as well as the morphology of any scar tissue, the system automatically tags locations where electrophysiological intervention is not feasible.

Figure 2:
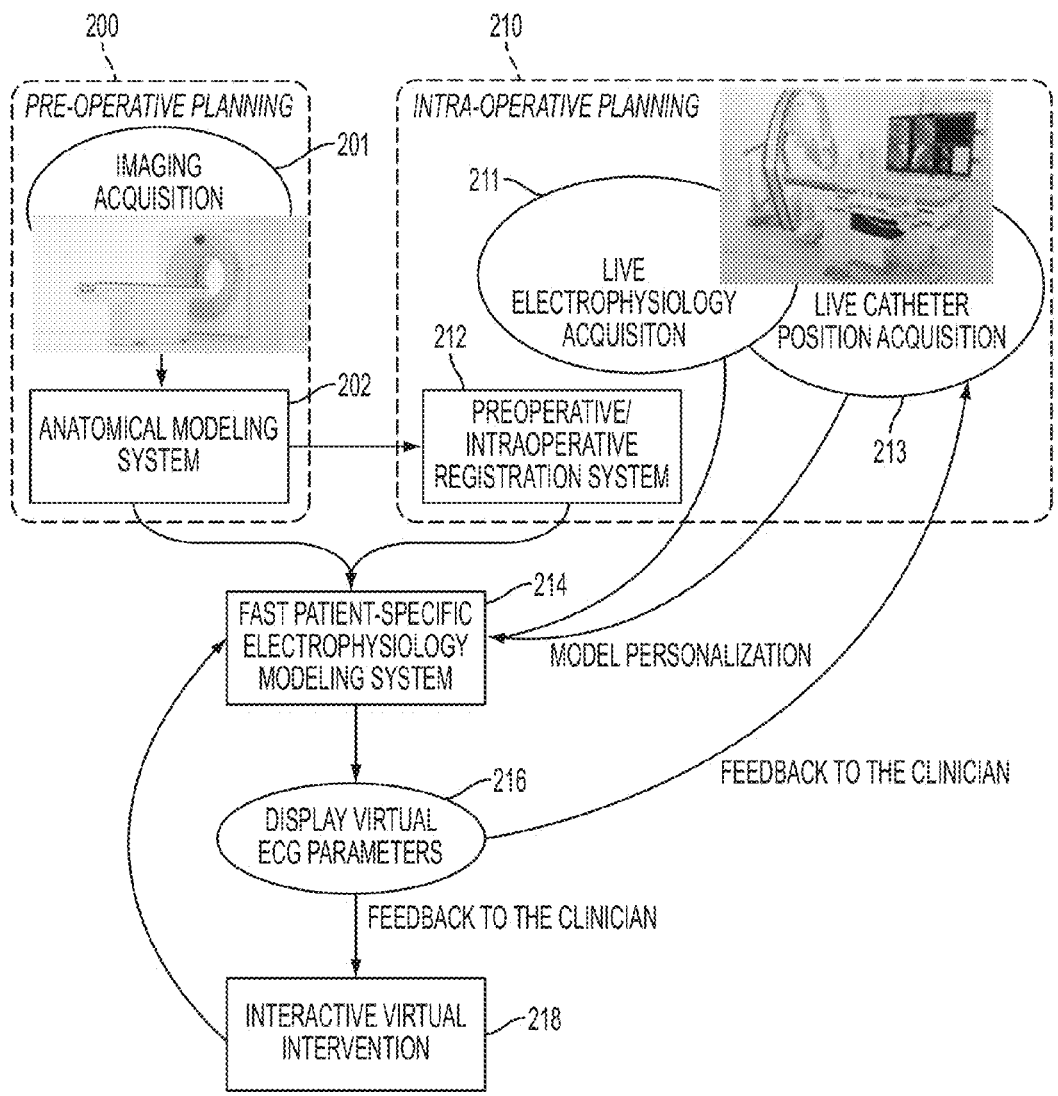
FIG. 2 illustrates a framework for patient-specific planning and guidance of electrophysiological intervention according to an embodiment of the present invention.

FIG. 2 illustrates a framework for patient-specific planning and guidance of electrophysiological intervention according to an embodiment of the present invention. As illustrated in FIG. 2, pre-operative planning 200 is performed prior to an electrophysiological intervention and intra-operative planning 210 is performed during the intervention. In the pre-operative planning phase 100, imaging acquisition 201 is performed to acquire preoperative cardiac images and an anatomical modeling system 202 automatically estimates an anatomical model from preoperative cardiac images. Any imaging modality can be used at this stage, provided the heart is entirely visible (e.g. CT, rotational angiography (DynaCT), MRI, US, etc.). If no preoperative imaging data is available, generic, disease-specific anatomies can be employed. If the patient is suitable for MRI study, MRI imaging of myocardium scar can be performed to estimate the extent of the scar tissue and border zone (damaged but functional cells), and this information is then mapped onto the anatomical model. Similar information can be acquired from other imaging modalities, such as CT perfusion for example. If available, CT angiography allows for imaging of the coronary veins, such that the patient's coronary venous morphology can be assessed and mapped to the anatomical model. In the intra-operative planning phase 210, live electrophysiology acquisition 211 and liver catheter position acquisition 213 are performed, and a pre-operative/intra-operative registration system 212 registers the anatomical model into an intra-operative coordinate system. The registration is performed using positioning information provided by the angiography system and/or position fiducials provided by the electrophysiology system. The registered anatomical domain is given as input to a fast patient-specific electrophysiology modeling system 214. That fast patient-specific electrophysiology modeling system 214 computes cardiac electrophysiology based on pre-operative information and, if available, live electrophysiological measurements (e.g., intracardial ECG) and the positions of the pacing catheters, which are used for personalization of the EP model. From the computed EP, virtual ECG signals are generated and virtual ECG parameters are displayed 216, for example on a display device of a computer system. Interactive virtual electrophysiological interventions 218 (e.g. CRT, VT ablation) are implemented in silica using the fast patient-specific electrophysiology modeling system 214 and their effects are evaluated through clinically relevant, ECG-based parameters that are displayed (216) to provide feedback to the clinician. The outcome of several different virtual interventions can then be quantitatively compared. If the images allow, the system can guide the electrophysiologist in implementing the intervention, automatically identifying sites in the myocardium that cannot be reaches due to the presence of localized scar tissue or due to the anatomy of the coronary sinus. It is to be understood that the anatomical modeling system 202, the pre-operative/intra-operative registration system 212, the fast patient-specific electrophysiology modeling system 214, and the interactive virtual intervention 218 are implemented on one or more computer systems by a processor executing computer program instructions.

Figure 3:
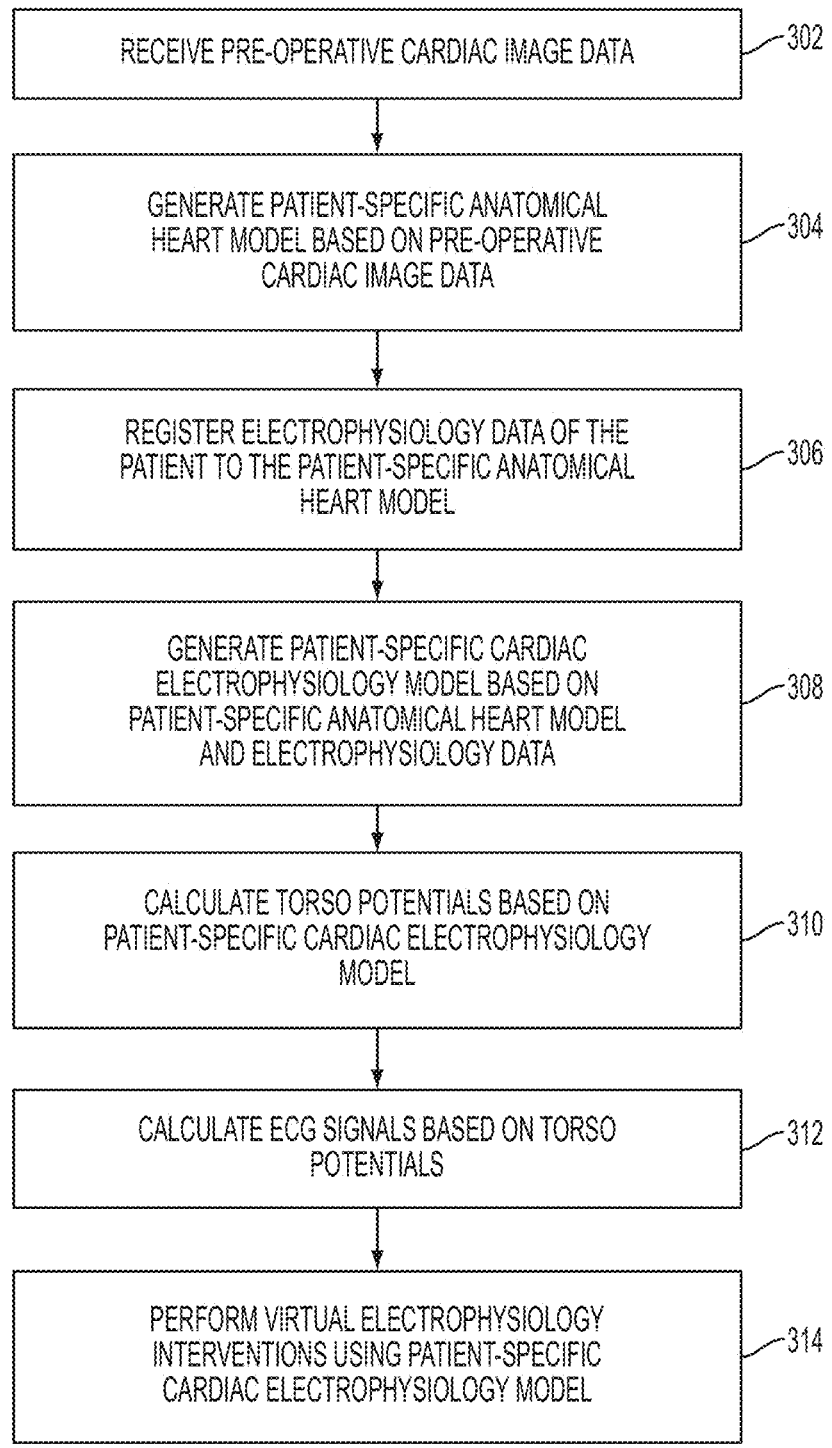
FIG. 3 illustrates a method for planning and guidance of electrophysiological interventions according to an embodiment of the present invention.

FIG. 3 illustrates a method for planning and guidance of electrophysiological interventions according to an embodiment of the present invention. The method of FIG. 3 transforms medical image data and electrophysiological measurements of a patient into simulated ECG signals and virtual ECG parameters for simulated virtual interventions. At step 302, pre-operative cardiac image data of a patient is received. The pre-operative cardiac image data can be acquired using any type of medical imaging modality, such as computed tomography (CT), three-dimensional rotational angiography, magnetic resonance imaging (MRI), ultrasound (US), etc., provided that the heart is entirely visible in the medical image data. In an advantageous implementation, the pre-operative cardiac image data includes three dimensional (3D) medical image data. The pre-operative cardiac image data can be received directly from an image acquisition device, such as a CT scanner, a C-arm image-acquisition device, an MRI scanner, or an US scanner, or the pre-operative cardiac image data can be received by loading previously stored cardiac image data of the patient.

Figure 4:
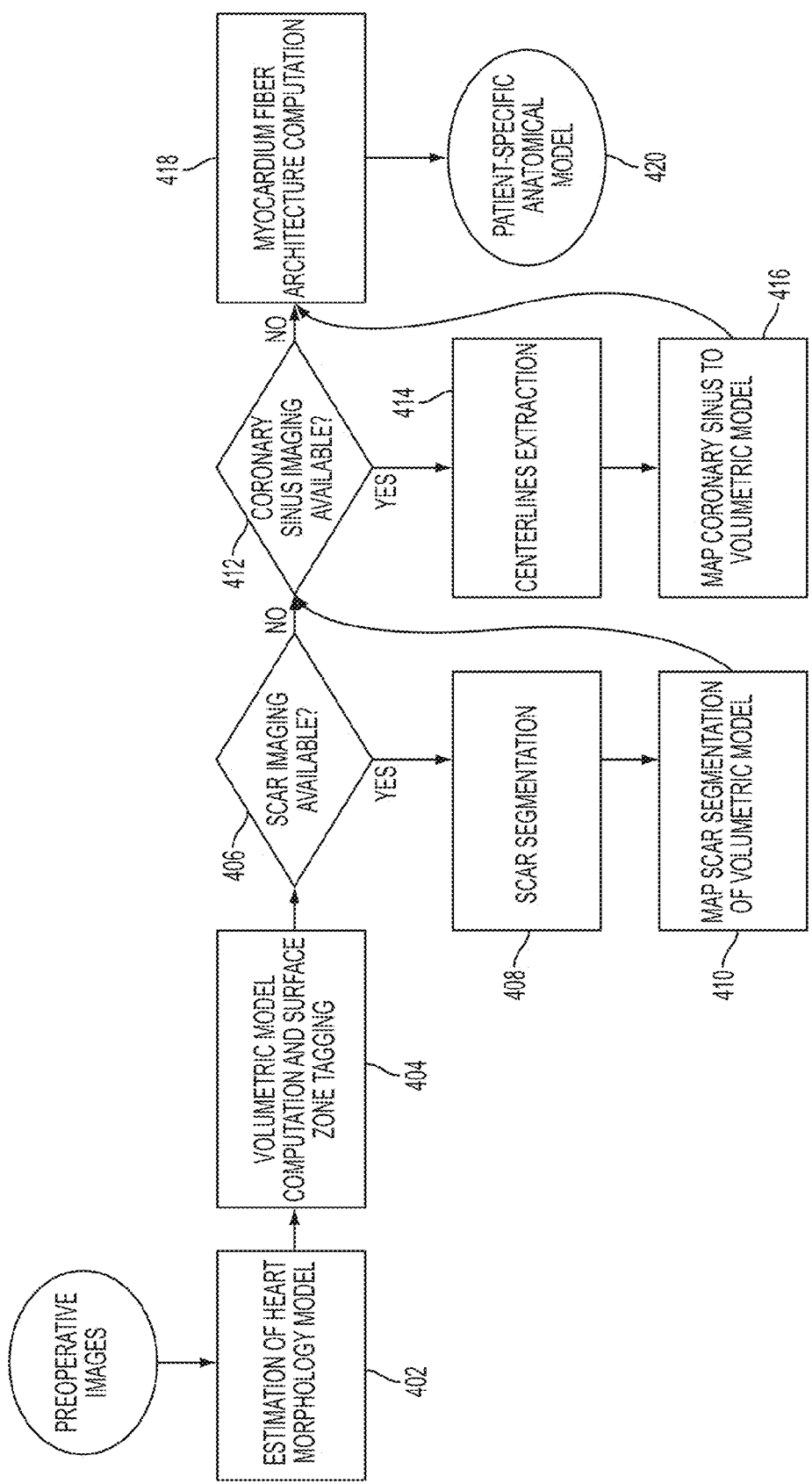
FIG. 4 illustrates a method for generating a patient-specific anatomical heart model according to an embodiment of the present invention.

At step 304, a patient-specific anatomical heart model is generated from the pre-operative image data of the patient. According to a possible implementation, this step can be performed in a pre-operative planning stage and the resulting patient-specific anatomical model can be stored in a memory or storage of a computer system until the time of the patient's intervention. Alternatively, this step can be performed at the beginning of or immediately prior to the patient's intervention. FIG. 4 illustrates a method for generating a patient-specific anatomical heart model according to an embodiment of the present invention. The method of FIG. 4 transforms pre-operative cardiac image data to generate a patient-specific anatomical model of the patient's heart. The method of FIG. 4 can be used to implement step 304 of FIG. 3.

Referring to FIG. 4, at step 402, a patient-specific heart morphology model is extracted from the pre-operative cardiac image data. The patient-specific heart morphology model can be a comprehensive geometrical model that represents the patient-specific heart morphology. In an advantageous embodiment, the patient-specific heart morphology model includes individual anatomical models representing the morphology of various heart components. The models are highly modular and can be customized depending on the application. The complete heart model can comprise the left ventricle (LV), left atrium (LA), left outflow tract, aortic root, pulmonary veins, right ventricle (RV), right atrium (RA), right outflow tract, RV neck, and veins. Papillaries and trabeculae can also be obtained, from CT images for instance. Each of these components can be used individually or jointly according to data availability and clinical application. In an exemplary embodiment, the LV and RV anatomical models estimated from the pre-operative cardiac image data are used. In a possible implementation, only the LV and RV are explicitly modeled. In another possible implementation, models for all of the heart chambers are extracted. It is also possible that the comprehensive model including all of the heart components is extracted. The modularity of this framework enables using images in which only part of the anatomy is visible. For example, pre-operative US images can be used to extract the LV model, but the present invention is not limited thereto.

The anatomical model for each heart component can be extracted individually. In particular, for each heart chamber, the heart chamber segmentation can be formulated as a two-step learning problem: anatomical structure localization and boundary delineation. In an advantageous embodiment, marginal space learning (MSL) can be used to apply machine learning to 3D object detection. The idea of MSL is not to learn a monolithic classifier directly in the full similarity transformation parameter space but to incrementally learn classifiers on marginal spaces. In particular, the detection of each heart chamber can be split into three problems: position estimation, position-orientation estimation, and position-orientation-scale estimation. A separate classifier is trained based on annotated training data for each of these estimation problems. Each classifier can be a probabilistic boosting tree (PBT) classifier trained based on annotated training data. The classifiers in the lower dimensional marginal spaces are used to prune the searching space efficiently. This object localization stage results in an estimated transformation (position, orientation, and scale) of the object (e.g., heart chamber).

After automatic object localization, the mean shape model of the object is aligned with the estimated transformation to get a rough estimate of the object shape. The shape is then deformed locally to fit the object boundary. Active shape models (ASM) can be used to deform an initial estimate of a non-rigid shape under the guidance of the image evidence and the shape prior. However, a non-learning based generic boundary detector, as used in conventional ASM applications, does not work effectively in heart chamber deformation due to the complex background and weak edges. Instead, a learning based boundary detector can be used to exploit more image evidences to achieve a robust boundary detection. Additional details regarding MSL-based heart chamber segmentation are described in U.S. Pat. No. 7,916,919, issued Mar. 29, 2011, and entitled "System and Method for Segmenting Chambers of a Heart in a Three Dimensional Image", United States Published Patent Application No. 2010/0040272, and United States Published Patent Application No. 2012/0022843, which are incorporated herein by reference.

At step 404, the patient-specific heart morphology model is fused into a single volumetric mesh representation and surface elements of the mesh are tagged into surface zones. For example, in the case of VT/VF ablation therapy, the patient-specific LV and RV anatomical models can be fused into a single anatomical model of the bi-ventricular myocardium. In particular, the LV and RV anatomies extracted in step 402 are fused into a single volumetric mesh representation. The LV and RV models can be fused into a single volumetric mesh representation, on which vertices are tagged into surface zones (LV endocardium, LV septum, RV endocardium, RV septum) according to the underlying anatomy of the estimated surface models. According to an advantageous embodiment, tetrahedral elements can be used to accurately represent the details of the bi-ventricular anatomy.

At step 406, it is determined if scar imaging data is available in the pre-operative cardiac imaging data. Certain types of medical imaging modalities, such as DE-MRI or CT perfusion, can be used to accurately localize scar tissue in a patient's heart. However, these types of medical image data may not be available for all patients. For example, because VT patient's typically wear implantable cardioverter-defibrillator (ICD) devices already, a pre-operative MRI often cannot be performed to quantify the extent of the scar tissue. Even in the case of MRI-compatible ICD devices, the artifacts generated by the ICD electrodes in MRI images can compromise identification of the scar tissue. If it is determined that scar imaging data is available for the patient, the method proceeds to step 408. If it is determined that scar imaging data is not available for the patient, the method proceeds to step 412.

At step 408, if the scar imaging data is available in the pre-operative cardiac imaging data, the scar tissue and grey zone tissue are segmented in the pre-operative cardiac imaging data. The grey zone tissue is a border zone surrounding the scar tissue that represents healing tissue. In an advantageous implementation, the scar tissue and border zone surrounding the scar tissue can be segmented by detecting myocardial borders of the heart in a sequence of image data (e.g., cine DE-MRI data) taken over multiple cardiac phases, and then classifying the detected myocardial borders as viable tissue or non-viable tissue (i.e., scar tissue) using a trained support vector machine (SVM), or other supervised learning technique. Such a method for segmenting scar tissue is DE-MRI image data is described in greater detail in U.S. Pat. No. 7,668,354, which is incorporated herein by reference.

At step 410, the segmented scar tissue and surrounding border zone is mapped to the volumetric mesh representation generated at step 404. For example, the tetrahedra shape of the volumetric mesh representation of the fused LV and LA can be locally modified to match the boundaries of the segmented scar tissue and border zone.

At step 412, it is determined if coronary sinus imaging data is available. Certain types of imaging modalities, such as DynaCT, CT angiography, and MR, can provide imaging of the coronary arteries and veins. If such image data is available, the method proceeds to step 414. If such image data is not available, the method proceeds to step 418.

At step 414, if coronary sinus imaging data is available in the pre-operative cardiac image data, centerlines of the coronary sinus are automatically extracted from the image data. The method for coronary artery centerline extraction described in United States Published Patent Application No. 2013/0216110, which is incorporated herein by reference, can be used to extract the centerlines of the coronary sinus.

At step 416, the coronary sinus is mapped to the volumetric mesh representation generated at step 404. In an advantageous implementation, tetrahedra in the anatomical model belonging to the coronary sinus are tagged based on their distance from the extracted centerlines of the coronary sinus.

At step 418, a model of myocardium fiber architecture is generated based on the patient's heart geometry. In one embodiment, the model of fiber orientation may be computed directly from the anatomical model using a rule-based method. A generic model of myocardium fiber architecture that includes fiber and fiber sheets is computed. A rule-based strategy is followed to generate the fiber architecture to cover the entire bi-ventricular myocardium from apex to valves. Below the basal plane, which is identified automatically using point correspondences of the initial triangulations of the anatomical model, the fiber elevation angle $\alpha$, i.e. their angle with respect to the short axis plane, varies linearly across the myocardium, e.g., from −70 on the epicardium to +70 on the endocardium (values that can be defined by the user). Similarly, the sheet direction, which is defined by the angle $\beta$ with respect to the outward transmural axis, varies transmurally, e.g., from +45 on the epicardium to −45 on the endocardium (values that can be defined by the user). α and β are computed for each point of the volumetric bi-ventricular myocardium mesh between the apex and basal plane based on the geodesic distance to the endocardia and epicardia identified by the facet tags: $\alpha=(d_{epi}\alpha_{endo}+d_{endo}\alpha_{epi})/(d_{endo}+d_{epi})$, where $d_{epi}$, $d_{endo}$, $\alpha_{epi}$, and $\alpha_{endo}$ are the distances and angles at the endocardium and epicardium, respectively. The fiber and sheet orientations are then fixed around each valve. In particular, fibers are longitudinal around the aortic valve and tangential around the mitral, tricuspid, and pulmonary valves, and sheet normals are oriented towards the barycenter of the valves. The local orthonormal basis is then interpolated from the basal plane to the valve, first by following the myocardium surface, then throughout the myocardium thickness. For orthonormality preservation, the interpolation can be performed using a Log-Euclidean framework.

Figure 5:
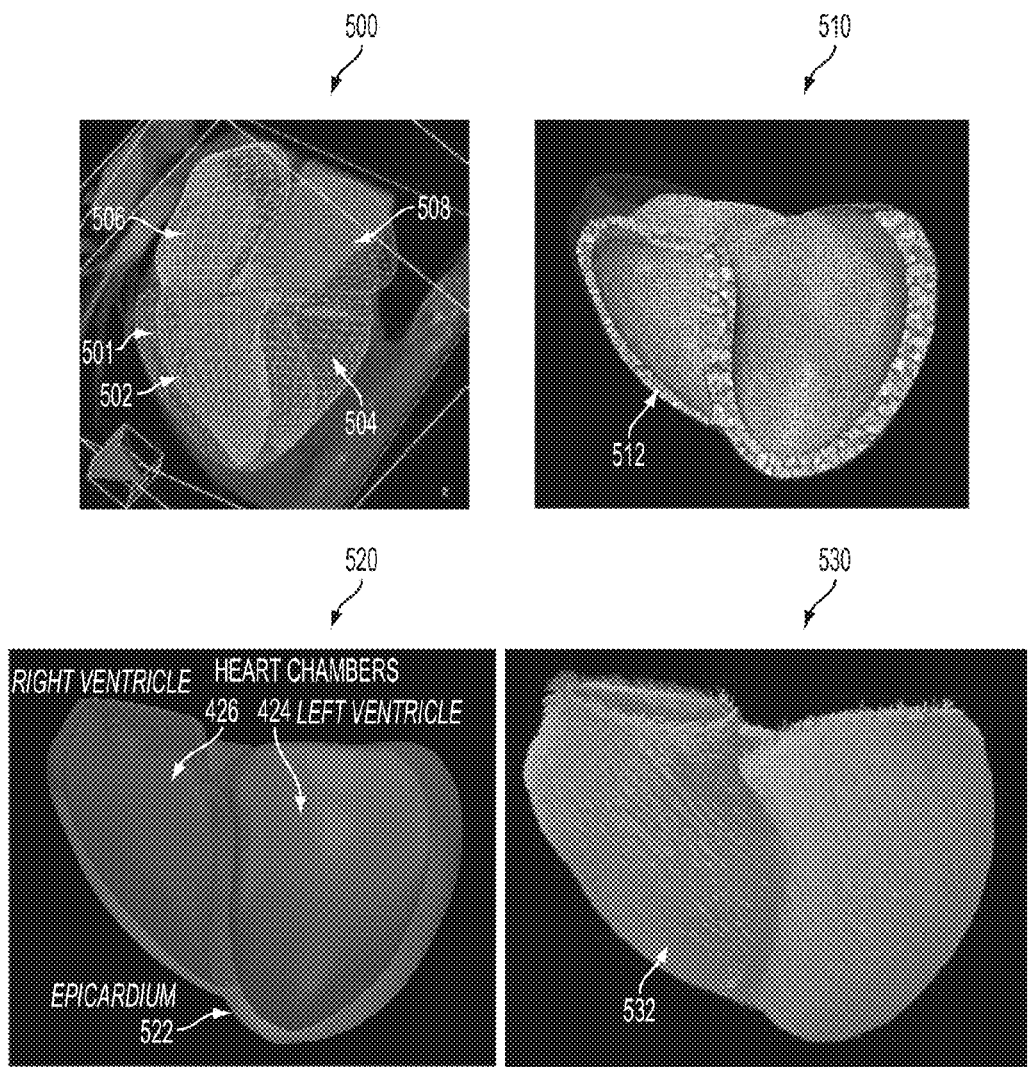
FIG. 5 illustrates exemplary results for extracting a patient-specific anatomical model.

In another embodiment, if in-vivo diffusion tensor (DT) MR images are available, DT MR images of the patient's cardiac fibers can be directly mapped to the anatomical model through image registration. In this case, the DT MR image is non-linearly registered to the medical image in which the LV and RV models are detected. The resulting transformation is used to deform the tensor field in the DT MR image towards the anatomical model. The Finite Strain method, the details of which are described in Peyrat et al., "A Computational Framework for the Statistical Analysis of Cardiac Diffusion Tensors: Application to a Small Database of Canine Hearts", *IEEE TMI*, 26(11):1500-1514, 2007, which is incorporated herein by reference, is used to reorient the tensors once the tensors are registered to the anatomical model. It is also possible, that an atlas of fiber architecture is available and the atlas is registered to the patient-specific anatomical model using standard image registration techniques At step 420, the patient-specific anatomical model is output. The patient-specific anatomical model generated in steps 402-418 is a patient-specific volumetric mesh representation of at least a portion of the heart (e.g., the bi-ventricular myocardium) that includes segmented scar tissue of the patient, if available, the coronary sinus, if available, and a patient-specific model of ventricular myocardium fiber architecture. The patient-specific anatomical model can be output by displaying the patient-specific anatomical model, for example, on a display device of a computer system. The patient-specific anatomical model can also be output by storing the patient-specific anatomical model on a memory or storage of a computer system. FIG. 5 illustrates exemplary results for extracting a patient-specific anatomical model. As illustrated in FIG. 5, image 500 shows patient-specific anatomical models of the left ventricle epicardium 501, left ventricle endocardium 502, right ventricle 504, left atrium 506, and right atrium 508, automatically extracted from 3D CT image data. Image 510 shows a fused volumetric anatomical mesh 512 resulting from fusing the left ventricle epicardium, left ventricle endocardium, and right ventricle anatomical models. Image 520 shows exemplary results of automatic mesh tagging of the volumetric mesh. In particular, surface elements of the volumetric mesh in image 520 are tagged into surface zones of epicardium 522, left ventricle 524, and right ventricle 526. Image 530 shows exemplary results of generating the patient-specific model of the ventricular myocardium fiber architecture 532.

Returning to FIG. 3, at step 306, electrophysiology (EP) data of the patient is registered to the patient-specific anatomical model. The EP data of the patient can be pre-operative EP data or intra-operative EP data. The use of pre-operative EP data allows a patient-specific cardiac EP model to be generated and virtual electrophysiological interventions to be performed for pre-operative planning independent of any actual intervention procedure being performed. The use of intra-operative EP data allows a patient-specific cardiac EP model to be generated and virtual electrophysiological interventions to be performed to guide an electrophysiological intervention in real-time or near real-time. The EP data of the patient can include one or more of pre-operative or intra-operative ECG measurements (12 lead, standard, etc.), endocardial mappings, and body surface mappings (BSM). Pre-operative diagnostic endocardial mappings can be registered to the patient-specific anatomical model manually or using spatial fiducials provided by the tracking capabilities of the electrophysiological mapping system. Endocardial mapping systems often provide 3D markers of key anatomical landmarks, such as the aortic valve, LV apex, etc. These landmarks are used to compute a 3D rigid transformation using the iterative closest point (ICP) method to register the endocardial mappings to the patient-specific anatomical hear model. Intra-operative endocardial mappings can be registered to the patient-specific anatomical model manually, using spatial fiducials, or by registering the patient-specific anatomical model to an intra-operative image (e.g., DynaCT or ultrasound) acquired during the intervention. ECG measurements can be registered by mapping the lead locations to the patient-specific anatomical model. BSM can be registered by back-projecting body surface potentials to locations in the patient-specific anatomical heart model.

At step 308, a patient-specific cardiac electrophysiology (EP) model is generated based on the patient-specific anatomical model and the EP data of the patient. The patient-specific cardiac EP model is a computational model of cardiac electrophysiology, the parameters of which are estimated based on the registered anatomical heart model and pre-operative or intra-operative EP measurements of the patient in order to personalize the patient-specific cardiac EP model for the patient.

According to an advantageous embodiment, virtual ECG parameters (VECGP) are estimated. These advanced measurements can be interactively computed based on patient-specific pre-operative image data and, if available, intraoperative measurements. In order to assess the effects of localized myocardial procedures on clinically relevant ECG-based values, embodiments of the present invention use the patient-specific cardiac EP model, once it has been personalized, to reconstruct VECGP for various simulated electrophysiological intervention procedures. Parameters of interest for the VECGP include, but are not limited to, the ECG trace, QRS duration, QRS morphology, and electrical axis.

If the pre-operative image data allows the morphological reconstruction of the patient-specific coronary sinus, as well as the identification of any scar tissue in the myocardium, maps of candidate locations for electrophysiological interventions, automatically excluding sites that art not feasible due to that presence of localized scar tissue or not reachable due to the vascular morphology. Such maps of candidate locations for electrophysiological interventions can be displayed sequentially, or selectively, to the electrophysiologist to provide guidance to the electrophysiologist during an intervention. The method described herein for calculating cardiac EP according to an advantageous embodiment of the present invention is fast and computationally efficient, which enables intraoperative update of the VECGP in near real time.

The personalization of the patient-specific cardiac EP model for the patient can also be seen as fitting the cardiac electrophysiology model to the patient-specific anatomical model and the pre-operative or intra-operative patient-specific EP data. The patient-specific EP measurements can include one or more of electrocardiograph (ECG) measurements (e.g., standard, 12 lead, etc.), an endocardial mapping, and BSM. When intra-operative EP measurements are used to personalize the patient-specific cardiac EP model, a current position of a pacing catheter can also be input.

Figure 7:
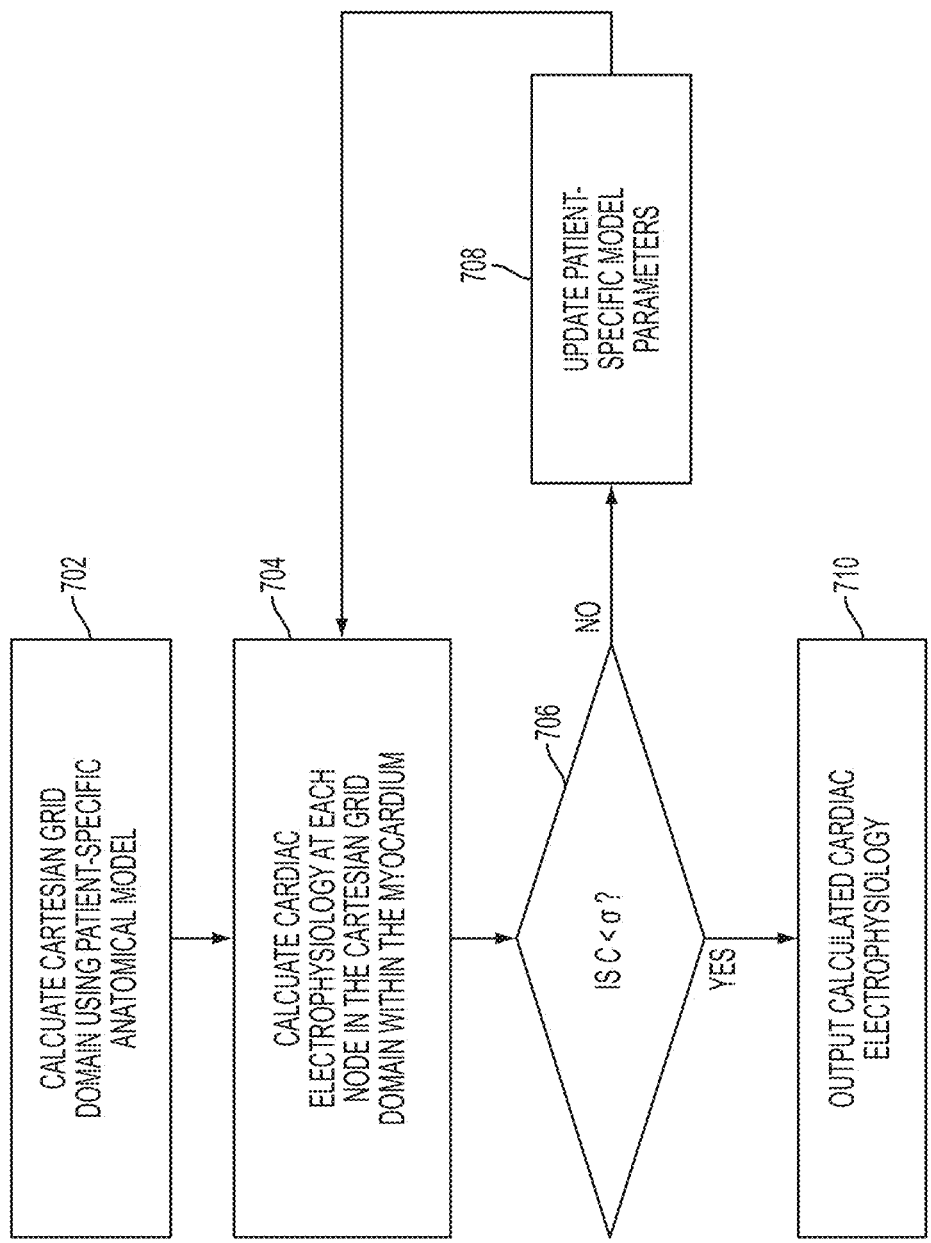
FIG. 7 illustrates a method for generating a patient-specific computational model of cardiac electrophysiology according to an embodiment of the present invention.

FIG. 7 illustrates a method for generating a patient-specific computational model of cardiac electrophysiology according to an embodiment of the present invention according to an embodiment of the present invention. The method of FIG. 7 transforms a patient-specific anatomical heart model and patient-specific EP measurements acquired during either pre-operatively or during an intervention into a patient-specific computational model of cardiac electrophysiology. The method of FIG. 7 can be used to implement step 308 of FIG. 3.

Figure 8:
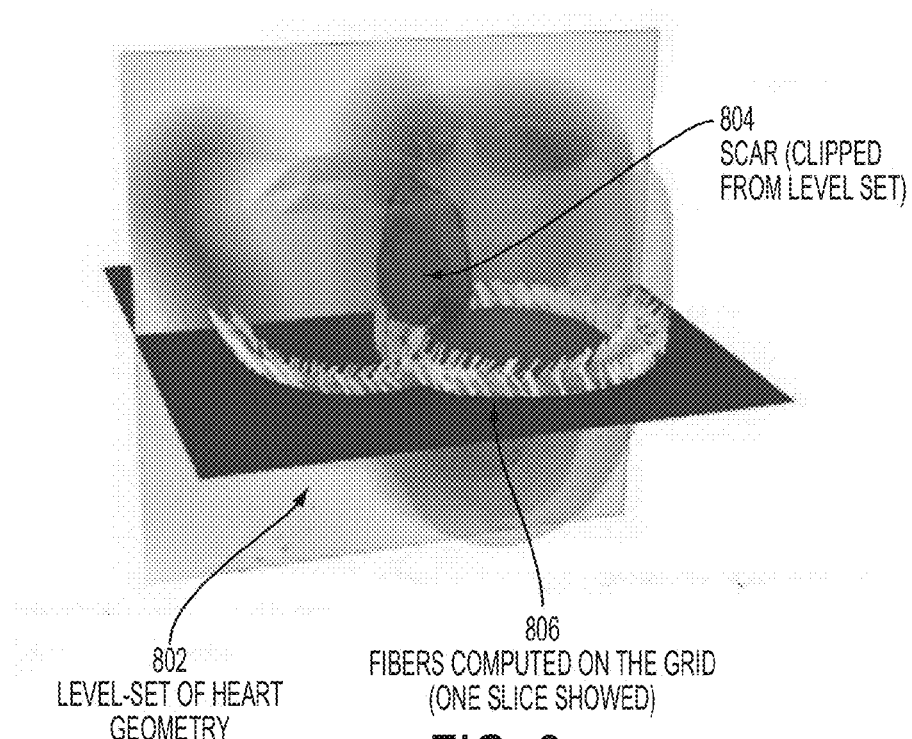
FIG. 8 illustrates an exemplary Cartesian grid domain for cardiac electrophysiology computation.

Referring to FIG. 7, at step 702, a Cartesian grid domain for electrophysiology computations is calculated using the registered patient-specific anatomical heart model. A Cartesian grid, possibly with unequal and spatially varying spacing, is first generated in a bounding box surrounding the anatomical model. Grid spacing can be defined by the user or fixed in the system. A level-set representation is then calculated from the patient-specific anatomical mesh as follows. For every node x of the grid, the shortest distance to the anatomical model mesh is calculated, and assigned to that node. In an advantageous embodiment, nodes inside the myocardium are defined by positive distances, and nodes not inside the myocardium are defined by negative distances. The opposite convention can be utilized as well without any modification. Nodes at myocardium, endocardia, and epicardium are tagged as such, as well as septal nodes. Available scars and border zones are also reported in the domain through additional level-set information. Fiber orientation f(x) are mapped to each node using rasterization techniques or recomputed from the mapped endocardial and epicardial zones. A diffusion coefficient D(x) and an action potential duration APD(x) is assigned to every myocardial node x of the Cartesian grid. Cell model parameters can also be mapped spatially at each node. FIG. 8 illustrates an exemplary Cartesian grid domain for cardiac electrophysiology computation. As shown in FIG. 8, the domain is represented using a signed level-set representation 802 of the registered anatomical model. Available scar information is clipped from the level-set representation 802 of the registered anatomical model and mapped as an additional level-set 804. Fiber orientation 806 (shown on one slice) is specified at each node of the domain.

Returning to FIG. 7, at step 704, cardiac electrophysiology is calculated at each node of the Cartesian grid domain within the myocardium. According to an advantageous embodiment of the present invention, cardiac electrophysiology is calculated at each node within the myocardium using the Lattice-Boltzmann Method for Electrophysiology (LBM-EP) to solve a cardiac electrophysiology model at each node. The cardiac electrophysiology model calculates the variation of the transmembrane potential v(x,t) over time according to the mono-domain equation:

$$\frac{dv(x,t)}{dt} = R(x,t) + \nabla \cdot D(x)K(x)\nabla v(x,t), \quad (1)$$

where R(x,t) is a reaction term describing the cellular mechanisms giving rise to the action potential, D(x) is the local diffusivity to be estimated from the patient-specific data, K(x) is the anisotropy matrix defined by $(1-\rho)f(x)f(x)^T+\rho Id$, $\rho$ being the ratio between the cross-fiber diffusivity and the fiber diffusivity (typically $\rho=0.11-0.25$). It is also possible to use orthotropic or fully anisotropic tensors K(x) for improved characterization of the fiber architecture.

The choice of the reaction term R(x,t) depends on the cellular model of cardiac electrophysiology that is used. The method disclosed herein is modular in that it can handle any standard mono-domain models, such as, but not limited to the "Mitchell-Schaeffer model" proposed in Mitchell et al., "A Two-Current Model for the Dynamics of Cardiac Membrane", *Bulletin of Mathematical Biology*, 65(5):767-793, 2003, or the model proposed in Ten Tusscher, et al., "Cell Model for Efficient Simulation of Wave Propagation in Human Ventricular Tissue Under Normal and Pathological Conditions", *Physics in Medicine and Biology*, 51, pp 6141, 2006. For the Mitchell-Schaeffer model for instance, we have:

$$R(x,t) = \frac{h(x,t)v^2(x,t)(1-v(x,t))}{\tau_{in}} - \frac{v(x,t)}{\tau_{out}} + J_{stim}(x). \quad (2)$$

In this equation $J_{stim}(x)$ is an external stimulus current. In intraoperative intervention planning, when the electrophysiologist is pacing the heart at a given location, the position of the pacing catheter is tracked using an embedded tracking method (e.g., electromagnetic tracking, bi-plane image-based tracking, etc.), and the position of the pacing catheter returned by the embedded tracking method is used to add a stimulus current to the model through $J_{stim}(x)$ at the acquired position. Virtual pacing is achieved by adding $J_{stim}(x)$ at a spatial location chosen by the user or chosen automatically by the system. The amount of current that is added to the model is obtained from the catheter manufacturer specifications.

In Equation (2), h(x,t) is a gating variable that controls the state of the ion channels according to the following ordinary differential equation:

$$\frac{dh(x,t)}{dt} = \begin{cases} \frac{1-h(x,t)}{\tau_{open}} & \text{if } v(x,t) < v_{gate} \\ \frac{-h(x,t)}{\tau_{close}} & \text{otherwise} \end{cases}$$

Figure 9:
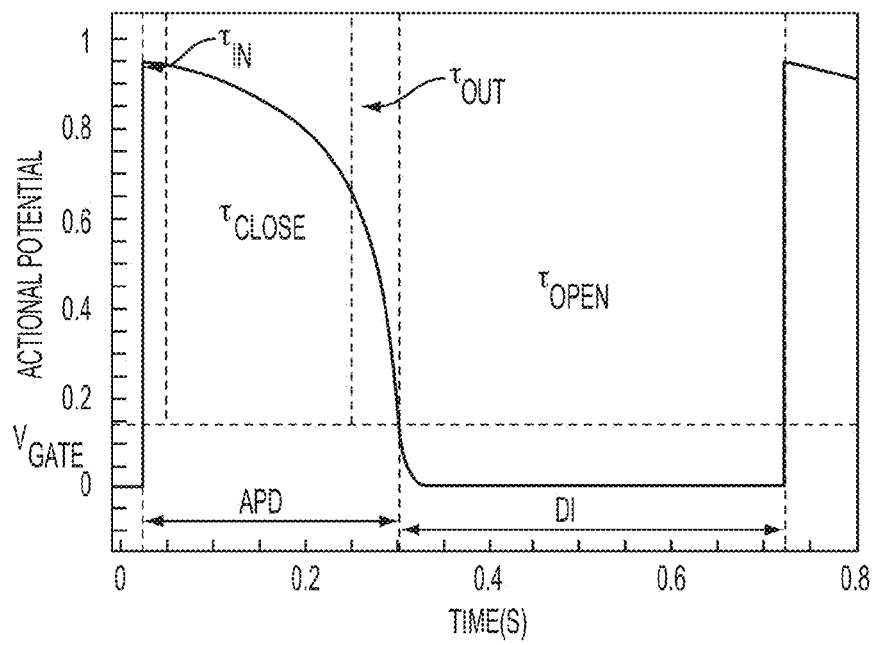
FIG. 9 illustrates relationships between model parameters and the shape of the action potential for the Mitchell-Schaeffer model.

$v_{gate}$ is a potential threshold, and $\tau_{in}, \tau_{out}, \tau_{open}$ and $\tau_{close}$ are parameters controlling the shape of the action potential. FIG. 9 illustrates relationships between model parameters and the shape of the action potential for the Mitchell-Schaeffer model. As shown in FIG. 9, the maximum action potential duration APD(x) is directly related to $\tau_{close}(x)$ according to the formula $APD_{max}(x)=\tau_{close}(x)\ln(\tau_{out}/(4\tau_{in}))$. In an advantageous embodiment of the present invention, only D(x) and $\tau_{close}(x)$ are estimated, the other parameters are kept constant to their default (i.e. nominal) values. However, it is also possible to implement this method to estimate these additional parameters as well.

Equation (1) is solved using the Lattice-Boltzmann method, referred to herein as LBM-EP. LBM-EP is a highly parallelizable algorithm to solve mono-domain electrophysiology equations. The LBM-EP algorithm is described in greater detail in United States Published Patent Application No. 2013/0226542, entitled "Method and System for Fast Patient-Specific Cardiac Electrophysiology Simulations for Therapy Planning and Guidance", which is incorporated herein by reference in its entirety. Contrary to standard finite-element methods, LBM-EP does not explicitly solve the reaction-diffusion equation but rather computes the "movement" of particles on a Cartesian grid, from which the reaction-diffusion behavior emerges. The particles can move according to fixed directions (or connectivities), with a certain probability. The algorithm includes two node-wise steps: streaming, which makes the particle jump from one node to another; and collision, which takes care of mass preservation and boundary conditions. It can be mathematically shown that this simple algorithm reproduces dynamics of the reaction-diffusion equation. In the method of FIG. 7, domain boundaries are represented as level-sets and tissue anisotropy is modeled. Since the method is node-wise, the algorithm is highly parallelizable. In an advantageous embodiment, the method can be implemented on a graphics processing unit (GPU), which enables near real-time and accurate cardiac electrophysiology computation during an intervention. In sinus rhythm, the electrocardiography model is computed with periodic stimulus at the septum to mimic the effects of the His bundle. The electrocardiography model can be initialized with high diffusivity coefficients on the endocardia to mimic the effect of Purkinje fibers, and lower diffusivity throughout the myocardium. These initial values are then updated in one or more subsequent iterations based on the patient-specific measurements received during the intervention to fit the cardiac electrocardiography model to the patient-specific measurements. It should be noted that since the framework relies on Cartesian grids, it is relatively simple to add more structural information in the model. For instance, Purkinje fibers, if available, can be added directly into the domain through rasterization. The His bundle and other electrophysiology bundles can be integrated similarly.

In an advantageous implementation, the outputs of calculating the cardiac electrophysiology at each node in the Cartesian grid domain within the myocardium at step 704 are i) a time varying 3D potential map; ii) a 3D map of depolarization times $t_{dep}(x)|v(x,t_{dep}-dt)<v_{gate}$, $v(x,t_{dep})>v_{gate}$; and a 3D map of repolarization times $t_{rep}(x)|v(x,t_{dep}-dt)>v_{gate}$, $v(x,t_{dep})<v_{gate}$. Additionally, other guidance maps, such as a 3D map of tissue diffusivity $D(x)$ and a 3D map of action potential duration $APD(x)$, can also be generated in step 704.

At step 706, it is determined if a cost function C that compares the calculated cardiac electrophysiology using the cardiac EP model with the measured EP data of the patient is less than a threshold σ. For example, pre-operative or intra-operative endocardial EP measurements can be mapped to the nodes of the computational domain and the cost function C can compare endocardial EP measurements with the calculated cardiac electrophysiology at each node of the computational domain. The cost function C can compare calculated and simulated ECG at the lead locations. For BSM, the cost function can compare back-projected body surface potentials at the nodes of the computational domain to the calculated cardiac electrophysiology or the calculated cardiac electrophysiology can be projected to the body surface and the cost function evaluated at the body surface. The cost function C can be evaluated base on any one of these EP measurements or a combination thereof.

In an exemplary embodiment, cost function C is evaluated based on the calculated depolarization times $t_{dep}(x)$, repolarization times $t_{rep}(x)$, and simulated ECG. In particular, after having calculated the depolarization times $t_{dep}(x)$ and repolarization times $t_{rep}(x)$ for each node in the myocardium, these values are compared with the pre-operative or intra-operative endocardial mapping measurements and ECG measurements for the patient. In an advantageous implementation, the cost function C can be expressed as:

$$C = \lambda_1 \|t_{dep}(x) - t_{measured\ dep}(x)\|_{L_2}^2 + \lambda_2 \|t_{rep}(x) - t_{measured\ rep}(x)\|_{L_2}^2 + \lambda_3 |QRS_{sim} - QRS_{ECG}| \quad (3)$$

where $t_{measured\ dep}(x)$ and $t_{measured\ rep}(x)$ are the depolarization and repolarization times determined from the pre-operative or intra-operative endocardial mapping measurements, $QRS_{sim}$ refers to the QRS of the simulated ECG calculated from the simulation of the cardiac electrophysiology performed in step 704, $QRS_{ECG}$ refers to the measured QRS of the pre-operative or intra-operative ECG measurements, and $\lambda_1$, $\lambda_1$, and $\lambda_1$ are weighting parameters. If the cost function C in Equation (3) is greater than the threshold σ, the method proceeds step 708. If the cost function C in Equation (3) is less than the threshold σ, the method proceeds step 710.

At step 708, when the cost function C is greater than the threshold σ, the patient-specific model parameters of the cardiac electrophysiology model are updated based on the patient-specific EP measurements. In particular, an inverse problem algorithm is utilized to automatically estimate the diffusivity $D(x)$ and action potential duration $APD(x)$ parameters of the cardiac electrophysiology model based on the pre-operative or intra-operative EP data. When using the cost function expressed in Equation (3), an inverse problem algorithm is utilized to estimate the diffusivity $D(x)$ and action potential duration $APD(x)$ parameters of the cardiac electrophysiology model based on the endocardial mapping measurements and ECG measurements for the patient. The aim of the inverse problem algorithm is to determine $D(x)$ and $APD(x)$ that minimize the cost function C. Examples of well known inverse problem algorithms that can be used to implement this minimization include trust regions, Kalman filtering, and variational approaches. To make the computation more efficient, $D(x)$ and $APD(x)$ can be defined zone-wise, with finer, smaller regions around a region of interest identified through the 12-lead ECG analysis. A multi-level, hierarchical approach can also be utilized.

As more patients are processed using this method, the range of parameters can be analyzed to provide better estimates for subsequent estimations (new patients, different pacing, etc.). Furthermore, a statistical model of the space of parameters $D(x)$ and $APD(x)$ with respect to heart geometry, scar extent, and stimulation protocol can be learned to further constrain the search space for future patients. Accordingly, once such a statistical model is learned, initial estimates for $D(x)$ and $APD(x)$ can be determined using the learned statistical model.

Once the patient-specific parameters $D(x)$ and $APD(x)$ of the cardiac electrophysiology model are updated, the method returns to step 704 and re-calculates the cardiac electrophysiology for each node within the myocardium using the updated model parameters. The method repeats steps 708, 704, and 706 until the cost function C is less than the threshold σ, indicating that the cardiac electrophysiology model is sufficiently fit to the patient-specific pre-operative or intra-operative EP measurements. This results in the patient-specific cardiac EP model for the patient.

At step 710, when the cost function C is less than the threshold σ, the cardiac electrophysiology values calculated at the last iteration of step 704 are output. In particular, calculated cardiac electrophysiology can include a time varying 3D potential map, a 3D map of depolarization times, a 3D map of repolarization times, a 3D map of tissue diffusivity, and 3D map of action potential duration. These maps can output by being displayed on a display device. In the case, in which the patient-specific cardiac EP model is personalized based on intra-operative EP data, these maps can be displayed in real-time or near real-time during the intervention in order to provide guidance as to the placement of a pacing catheter or an ablation catheter during the intervention. Furthermore, the calculated cardiac electrophysiology is further used in the method of FIG. 3 to calculate torso potentials and simulated ECG signals.

Returning to FIG. 3, at step 310, torso potentials are calculated based on the patient-specific cardiac EP model. The patient-specific cardiac EP model calculates the transmembrane potential $v(x,t)$ at each node within the myocardium. Once the transmembrane potential $v(x,t)$ is calculated, the extra-cellular potential $\Phi_e$ at each node can be calculated using a closed-form expression ($\Omega$ defines the computational domain; $|\Omega|$ is the number of elements therein):

$$\phi_e(x, t) = \frac{\lambda}{1+\lambda} \frac{1}{|\Omega|} \int_\Omega [v(y, t) - v(x, t)] dy$$

where $\lambda$ is a constant diffusion anisotropy ratio, $\lambda = D_i(x)/D_e(x)$, and $D_i$ and $D_e$ are intra- and extra-cellular diffusivity tensors. The extra-cellular potential $\phi_e$ is then mapped back to the epicardium surface mesh using tri-linear interpolation. Furthermore, the extra-cellular potentials are projected onto the torso surface using a boundary element method (BEM). The potential $\phi(x)$ at any point x of the thoracic domain can be calculated as:

$$\phi(x) = \frac{1}{4\pi} \int_{S_B} \phi_b \frac{r \cdot n}{\|r\|^3} dS_B - \frac{1}{4\pi} \int_{S_H} \left[ \phi_e \frac{r \cdot n}{\|r\|^3} + \frac{\nabla \phi_e \cdot n}{\|r\|} \right] dS_H$$

where r is the vector defined by x and the integration point, while $S_B$ and $S_H$ are the torso and epicardium surfaces, respectively. The body surface potential at the torso, $\phi_b$, can be expressed as a function of the extra-cellular potential $\phi_e$, which allows the potential to be calculated at any point on the torso. According to an advantageous implementation, a torso mesh can be segmented from the medical image data using machine learning algorithms and the body surface potential $\phi_b$ can be calculated for each vertex on the torso mesh.

At step 312, ECG signals are calculated based on the torso potentials. Based on the body surface potentials, which are computed for each vertex at the torso mesh, the potential all the standard ECG lead locations is estimated, resulting in simulated ECG signals. The VECGP can be calculated based on the simulated ECG signals. The simulated ECG signals and the VECGP can be output, for example, by being displayed by a display device of a computer system.

Figure 10:
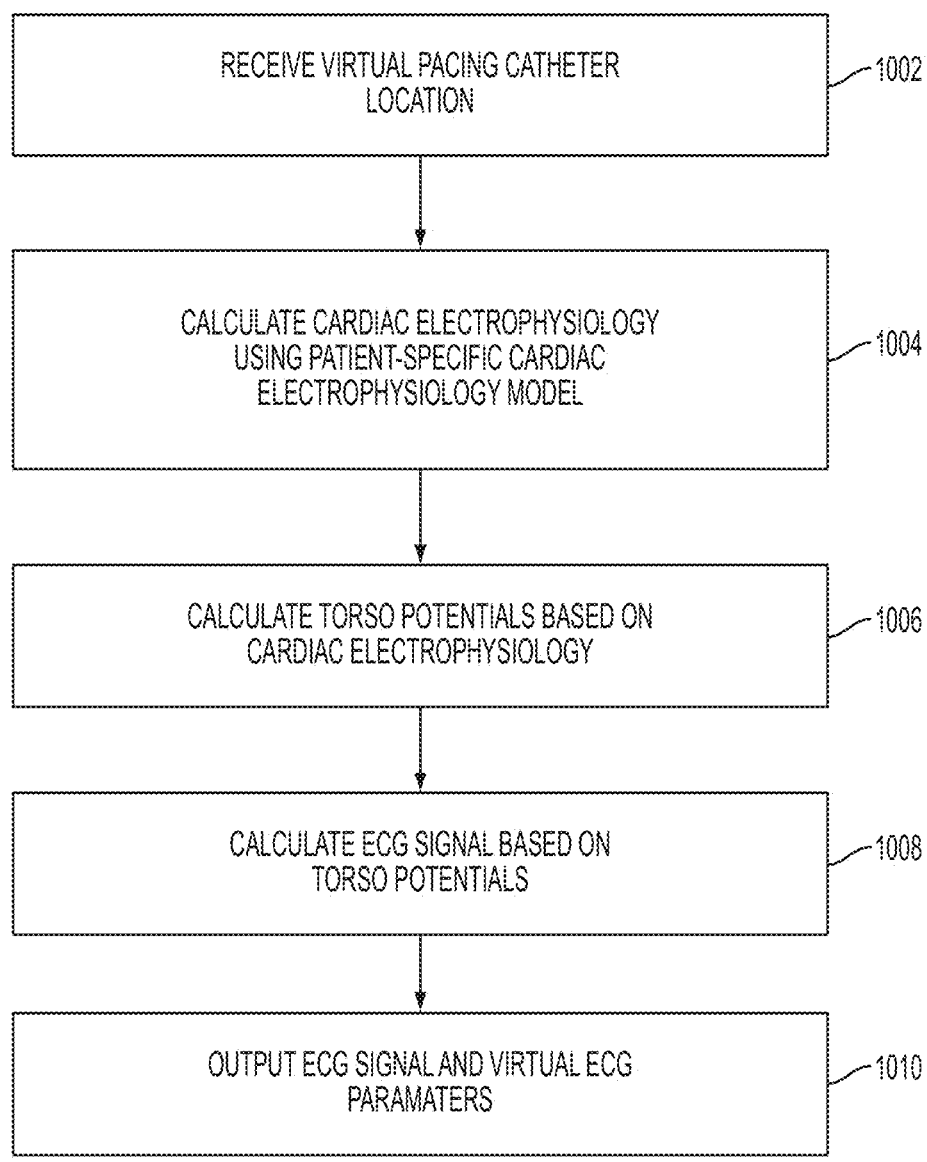
FIG. 10 illustrates a method for performing a virtual electrophysiological intervention according to an embodiment of the present invention.

At step 314, virtual electrophysiological interventions are performed using the patient-specific cardiac EP model. The virtual electrophysiological interventions can be used for pre-operative planning or intra-operative guidance. For each virtual electrophysiological intervention, a simulate ECG signal is generated that predicts that patient's ECG measurements after such an intervention, and the ECG signals and the VECGP are displayed. FIG. 10 illustrates a method for performing a virtual electrophysiological intervention according to an embodiment of the present invention. The method of FIG. 10 can be used to implement step 314 of FIG. 3.

Referring to FIG. 10, at step 1002, a virtual pacing catheter location is received. Once the cardiac electrophysiology model is personalized with patient-specific parameters, this patient-specific cardiac EP model is generative, and can be used to virtually simulate any electrophysiological intervention without actual testing on the patient. In a possible implementation, since the system is generative, the user (e.g., physician) can select one or more locations to virtually pace the heart, given the current estimate of the diffusivity map $D(x)$ and the action potential duration map $APD(x)$. The user can input a spatial location for a virtual pacing catheter, for example using an input device, such as a mouse, touch screen, etc., of a computer system to select a spatial location on the anatomical heart model or one of the cardiac electrocardiography maps generated by the patient-specific cardiac EP model. In an alternative implementation, systematic virtual pacing may be automatically applied by rasterizing the model, in order to detect optimal pacing locations. In particular, a sampling scheme can be used to automatically select virtual pacing locations, and a virtual electrophysiological intervention can be performed for each pacing location.

At step 1004, cardiac electrophysiology is calculated using the patient-specific cardiac EP model. In particular, a current $J_{stim}$ is added to the patient-specific cardiac EP model at the location of the virtual pacing catheter and the cardiac electrophysiology is computed over a period of time. The system allows for virtual ablation by locally setting the tissue diffusivity to 0 to mimic the ablated lesion.

At step 1006, the torso potentials are calculated based on the cardiac electrophysiology calculated at step 1004. As described above in connection with step 310 of FIG. 3, the torso potentials are calculated by first calculating the extra-cellular potential from the transmembrane potential calculated in the cardiac electrophysiology, and then calculating the body surface potential at various points on the torso based on the extra-cellular potential.

At step 1008, the simulated ECG signal is calculated based on the torso potentials. In particular, the ECG signal is generated using the torso potentials at the locations of the standard ECG lead. The ECG signal also provides the virtual ECG parameters (VECGP), which can be used to assess various virtual electrophysiological interventions.

At step 1010, the ECG signal and the virtual ECG parameters (VECGP) are output. The simulated ECG signal and the VECGP can be output by being displayed, for example, on a display device of a computer system. In an advantageous implementation, the simulated ECG signal and the VECGP can be displayed in real-time or near real-time during an electrophysiological intervention to provide inter-operative guidance. The simulated ECG signal and VECGP can also be output by being stored on a memory or storage device of a computer system.

The patient-specific virtual electrophysiological interventions can be performed for pre-operative planning or intra-operative guidance. When the patient-specific virtual electrophysiological interventions are used for real-time or near real-time intra-operative guidance during an interventional procedure, the patient-specific anatomical heart model of the patient can be registered to the coordinate system of intra-operative images used to guide the intervention procedure. Interventions, such as CRT and CT ablation procedures, are typically guided by a sequence of 2D fluoroscopic images which are acquired in real-time during the intervention. The patient-specific anatomical heart model extracted from the pre-operative cardiac image data is registered to the coordinate system of the fluoroscopic images. In one possible implementation, the patient-specific anatomical model can be manually registered into the angiography space (i.e., the coordinate system of the fluoroscopic images). For example, this registration can be performed manually by a physician using bi-plane fluoroscopic image acquisition (90 degrees between detectors) and a contrast medium injected into the patient to allow the physician to visualize the anatomy in the fluoroscopic images.

In another possible implementation, an intra-operative three-dimensional rotational angiography image of the patient's heart can be acquired using a C-arm image acquisition device. A C-arm image acquisition device rotates around a patient to acquire fluoroscopic images at different projection angles and reconstructs a 3D rotational angiography image from the set of 2D projections. Since the C-arm image acquisition device is also used to acquire the intra-operative fluoroscopic images used to guide the ablation procedure, the coordinate system of the 3D rotational angiography image is the same as the coordinate system of the intra-operative fluoroscopic images. In this case, a method for multi-modal model-based fusion is used to register the pre-operative anatomical model to the 3D rotational angiography image. In particular, a probability map of cardiac pericardium is computed from the rotational angiography image using a machine-learning algorithm, such as Marginal Space Learning (MSL). Additional details regarding MSL-based segmentation are described in U.S. Pat. No. 7,916,919, which is incorporated herein by reference. The preoperative surface mesh of patient's pericardium is then mapped to the rotational angiography coordinate system using an optimization algorithm that maximizes the integrated probability along the surface mesh. The resulting deformation is extrapolated to the volume domain by thin-plate spline interpolation. Finally, the preoperative volumetric model is registered by applying the dense deformation field. Myocardium fibers are reoriented accordingly by using the local Jacobian matrix of the deformation field.

In another possible implementation, if no intra-operative 3D imaging data is available, the volumetric anatomical model can be rigidly registered onto the intra-operative coordinate system using spatial fiducials provided by the tracking capabilities of an electrophysiological mapping system. Endocardial mapping systems often provide 3D markers of key anatomical landmarks, such as the aortic valve, LV apex, etc. These landmarks are used to compute a 3D rigid transformation using the iterative closest point (ICP) method to register the volumetric model to the intra-operative coordinate system.

In a situation in which no 3D rotational angiography data is available and no endocardial mapping fiducials are available for registering the pre-operative patient-specific anatomical model to the intra-operative coordinate system, external fiducials may be placed on the patient's chest during pre-operative and intra-operative image acquisitions. These fiducials can then be employed to calculate a rigid transformation to register the patient-specific anatomical model to the intra-operative image data. It is also possible that catheter fiducials may be available in the fluoroscopy images for pre-preoperative/intra-operative anatomical model registration.

When possible, the left atrium is used as a surrogate to drive the registration methods described in the previous points. This is achieved as follows: 1) a detailed left heart model including the LV and LA is estimated on the preoperative images; 2) the LA is then registered to the angiography space with any of the above mentioned implementations; 3) the LV "follows" the LA transformation as the two structures are anatomically attached to each other. That is, the transformation used to register the LA in the pre-operative anatomical model with the LA in the intra-operative coordinate system is then applied to register the entire patient-specific anatomical model.

Since the system and method described herein are modular, any pre-operative/intra-operative registration method can be utilized. It is also possible that a coupled imaging system, such as an X-ray/MRI set-up, can be employed to perform this registration. Further, any of the above described techniques can be utilized individually or jointly for improved accuracy. Although, the intra-operative images are described herein as fluoroscopic images, the present invention is not limited thereto. For example, embodiments of the present invention can similarly be applied to electrophysiological interventions under MRI or ultrasound guidance, as well.

Figure 6:
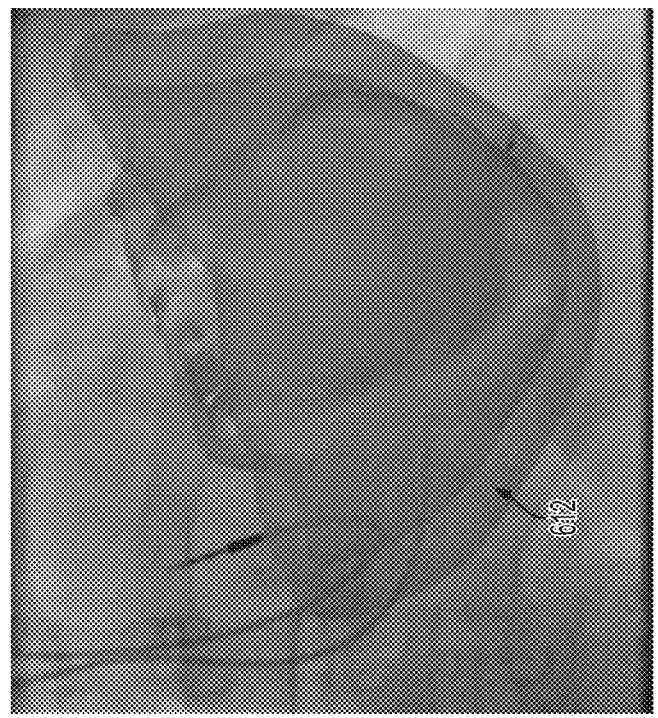
FIG. 6 illustrates exemplary results of registering a pre-operative patient-specific anatomical model to a coordinate system of intra-operative images.
Figure 6:
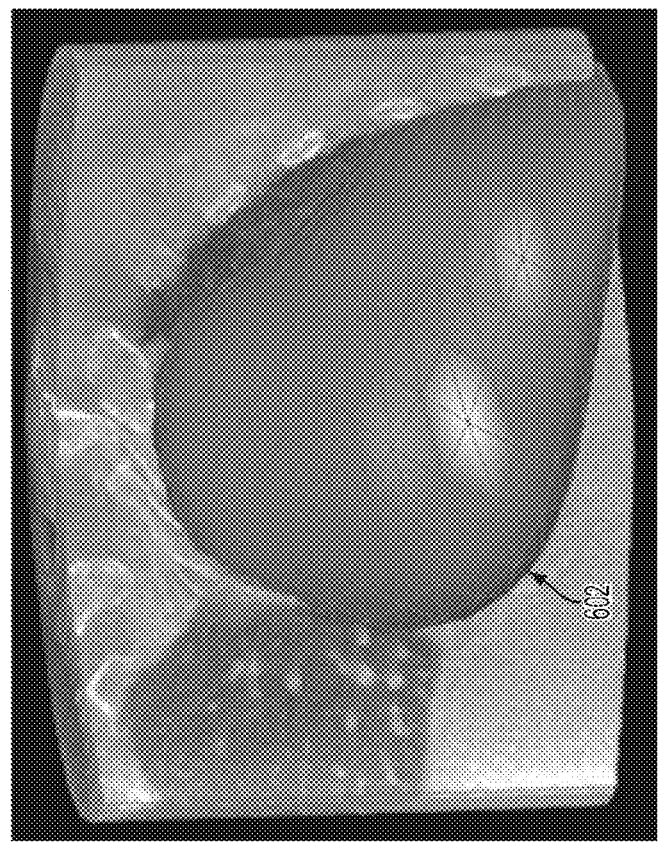

FIG. 6 illustrates exemplary results of registering a pre-operative patient-specific anatomical model to a coordinate system of intra-operative images. Image 600 of FIG. 6 shows a pre-operative patient-specific anatomical heart model 602 registered to a 3D intra-operative rotational angiography image. Image 610 if FIG. 6 shows a pre-operative patient-specific anatomical heart model 612 overlaid on an intra-operative 2D fluoroscopic image.

A retrospective dilated cardiomyopathy (DCM) patient who underwent CRT therapy was selected by the present inventors as a test case. The following pacing protocols were tested: sinus rhythm (base line), LV-RV stimulation, RV pacing, and LV triggered pacing with 40 ms delay. ECG response to the CRT pacing showed that the LV-triggered protocol offered optimal performances, while all other protocols actually worsened the cardiac function. That case is particularly challenging because despite being in the eligibility criteria, the patient did not respond to any pacing protocols, both in terms of QRS duration improvement and ultrasound evaluation. On the contrary, all protocols but LV-triggered yielded significantly worse cardiac function.

Figure 11:
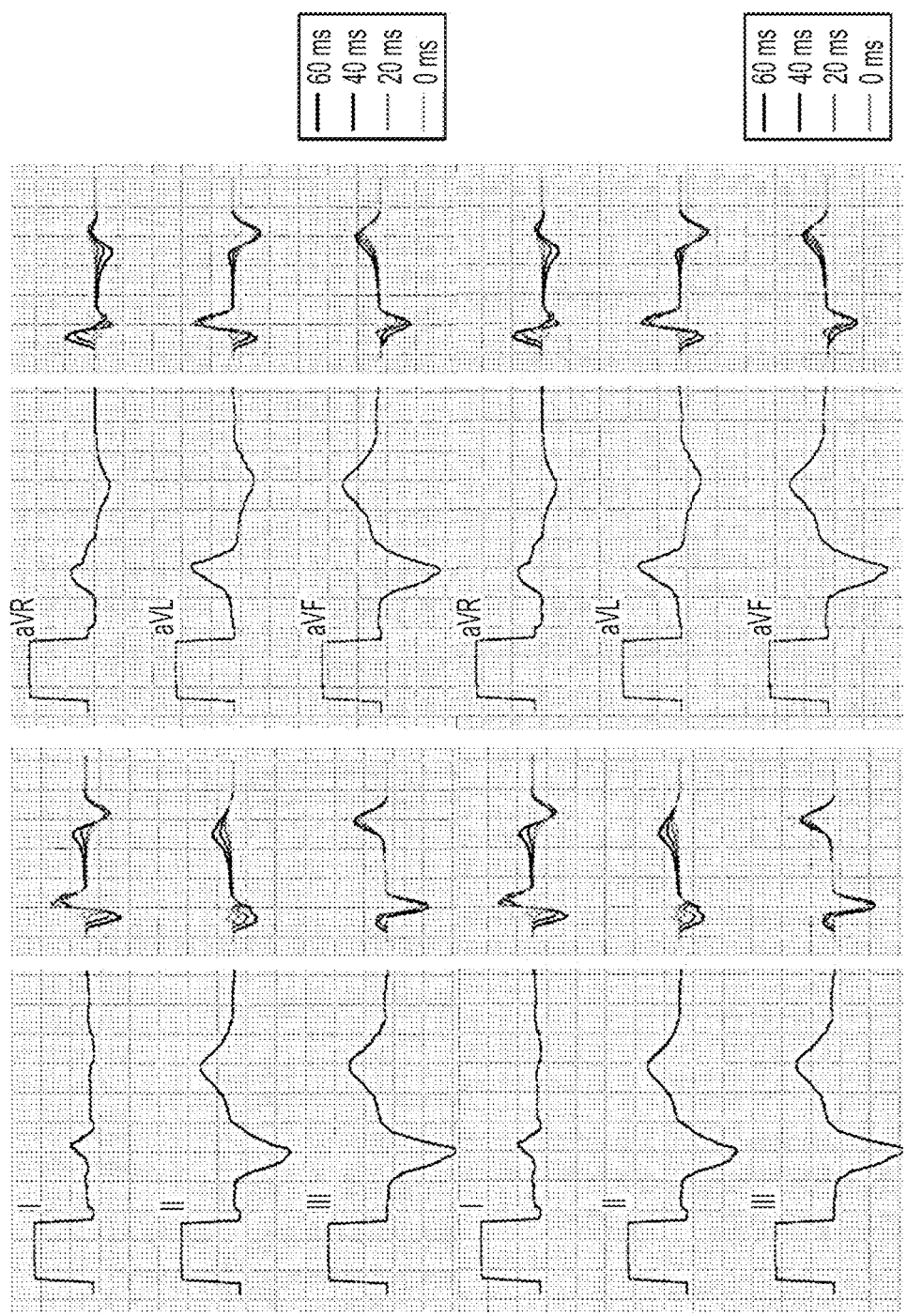
FIG. 11 illustrates measured and computed ECG limb lead signals for the right ventricle (RV) pacing protocol using different activation times.

The three different pacing protocols were simulated on the personalized heart model. FIG. 11 illustrates measured and computed ECG limb lead signals for the RV pacing protocol using different activation times. As shown in FIG. 11, the experiment with earliest pacing time (60 ms before natural activation) shows most agreement with measured curves, and the predicted QRS duration ($QRS_{RV}^C$=175 ms) matches the observed one closely ($QRS_{RV}^{meas}$=184 ms).

Figure 12:
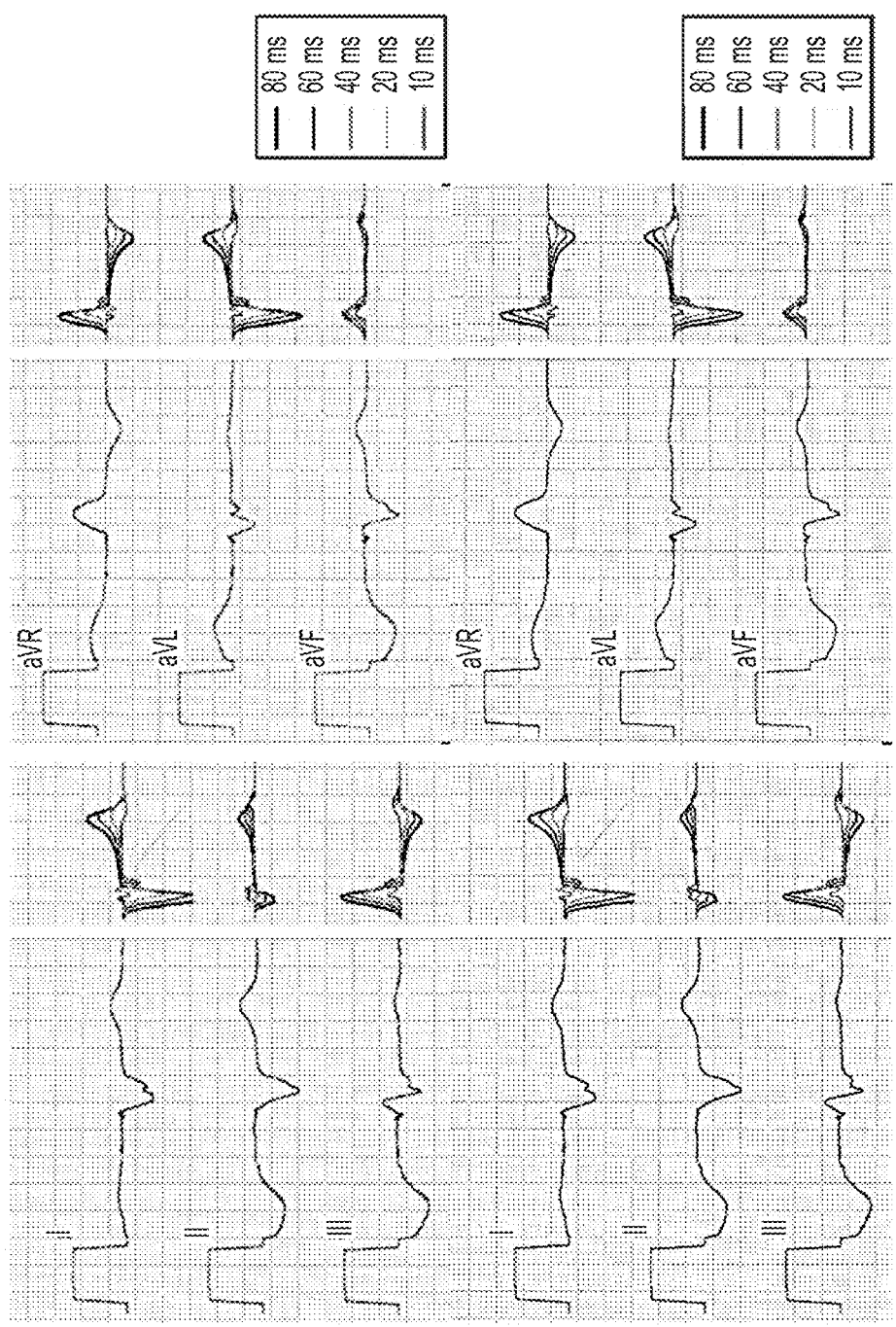
FIG. 12 illustrates measured and computed ECG signals for the bi-ventricular pacing protocol, again using different left ventricle (LV) pacing times before natural activation.

FIG. 12 illustrates measured and computed ECG signals for the bi-ventricular pacing protocol, again using different LV pacing times before natural activation. For all experiments, RV activation was fixed to 20 ms after LV activation. As shown in FIG. 12, even though the magnitudes of computed R and T waves do not relatively match the measured ones, wave directions are consistent with clinical data. The average computed QRS duration of $QRS_{Bi}^C$=120 ms was lower than the measured duration of $QRS_{Bi}^{mea}$=171 ms.

Figure 13:
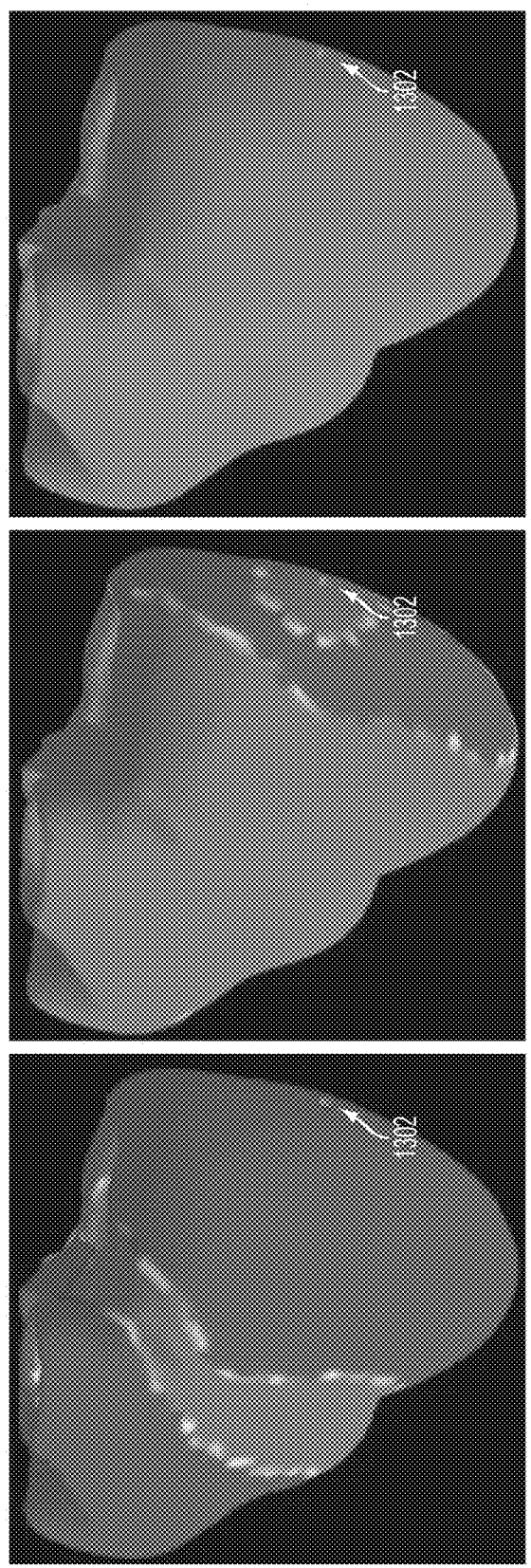
FIG. 13 illustrates exemplary results of the simulated electrophysiology over time.
Figure 14:
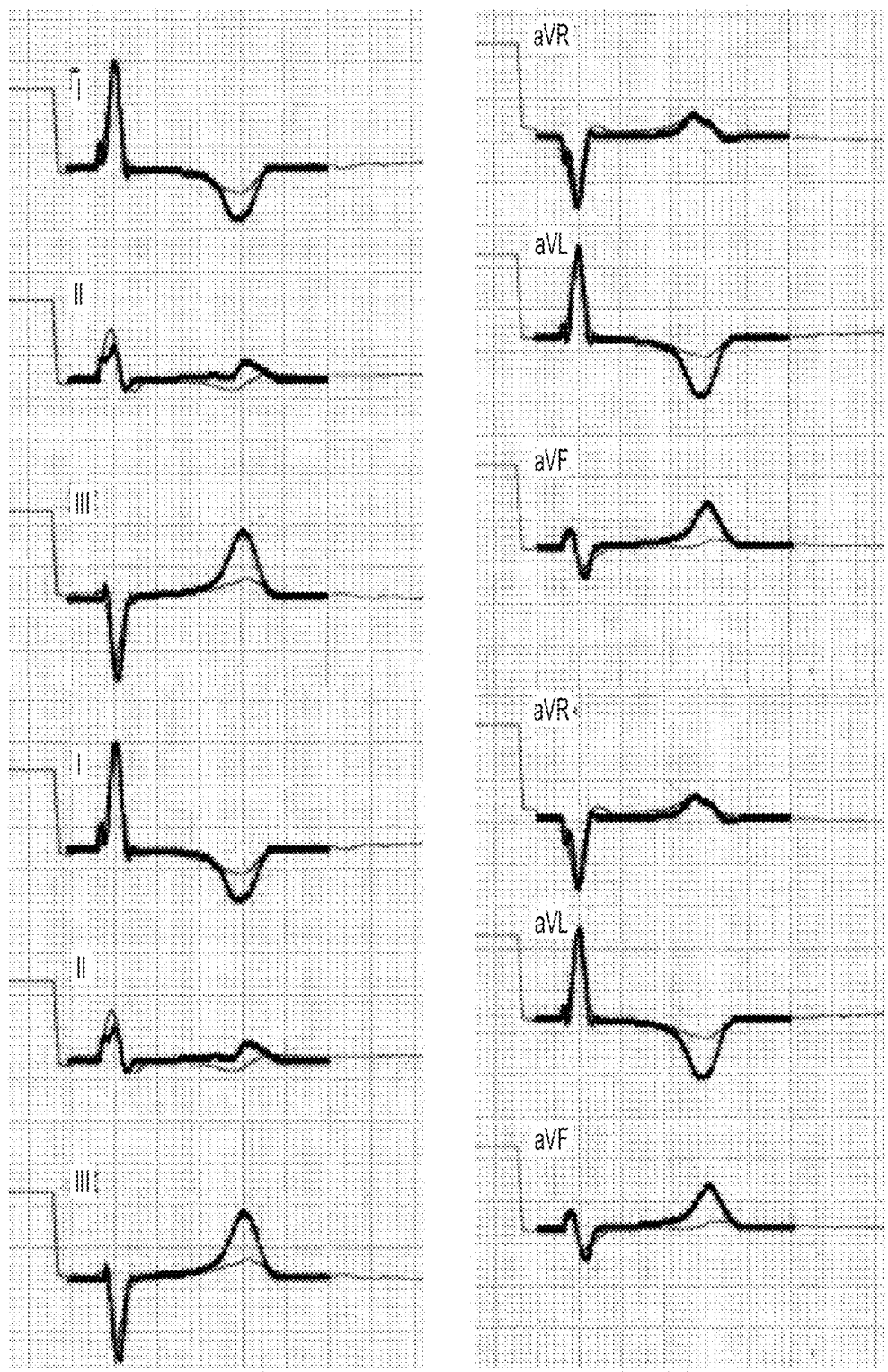
FIG. 14 illustrates an overlay of computed limb lead ECG curves on clinically acquired ECG signals for the LV pacing protocol.

For LV-triggered pacing, the lead was activated 40 ms after natural right ventricular pacing. FIG. 13 illustrates exemplary results of the simulated electrophysiology over time, which exhibits a clear fusion between the intrinsic electrical wave and the one created by the virtual LV lead 1302. Predicted QRS duration slightly improved with respect to the baseline ($QRS_{LV}^C$=108 ms), which is about 18 ms lower than the QRS duration observed in the patient ($QRS_{LV}^{meas}$=126 ms). FIG. 14 illustrates an overlay of computed limb lead ECG curves on clinically acquired ECG signals for the LV pacing protocol. As it can be seen from FIG. 14, the computed ECG captures the main features of the measured ECG.

Figure 15:
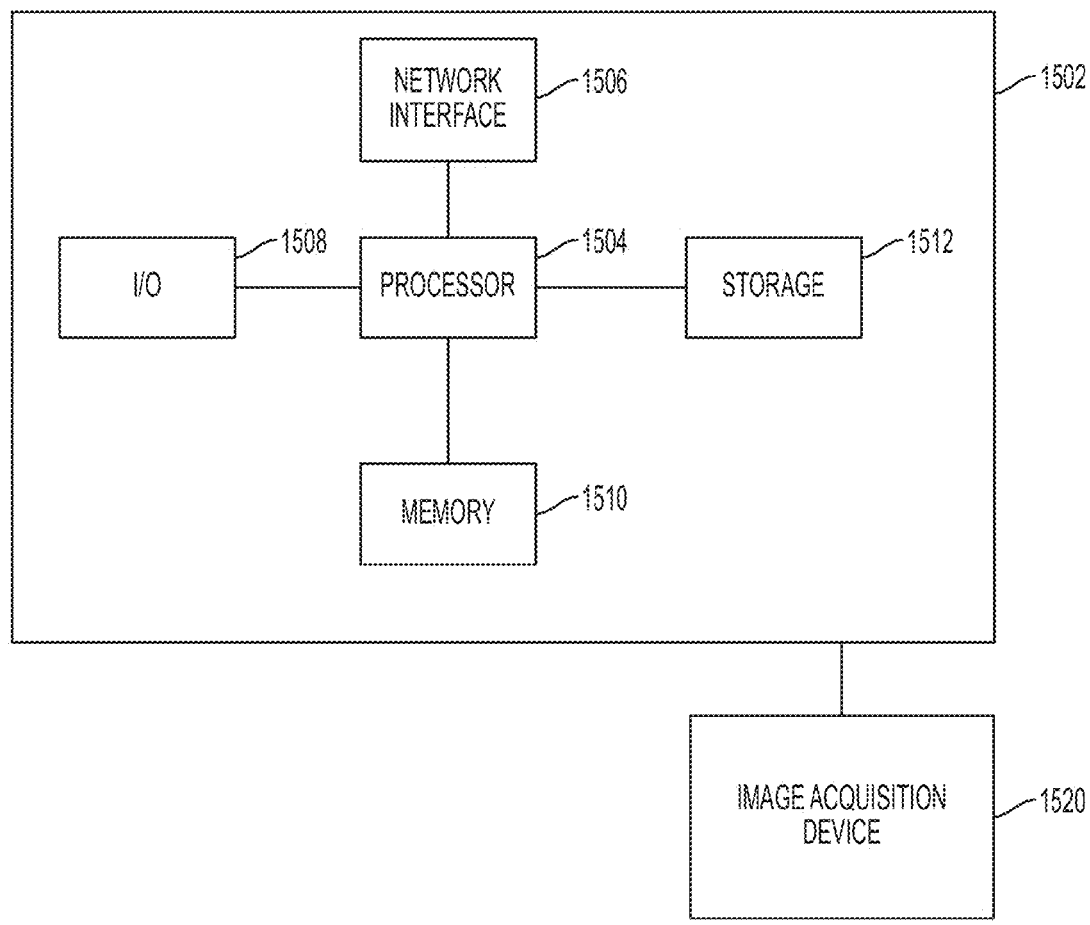
FIG. 15 is a high-level block diagram of a computer capable of implementing the present invention.

The above-described methods for patient-specific planning and guidance of electrophysiological interventions can be implemented on a computer using well-known computer processors, memory units, storage devices, computer software, and other components. A high-level block diagram of such a computer is illustrated in FIG. 15. Computer 1502 contains a processor 1504, which controls the overall operation of the computer 1502 by executing computer program instructions which define such operation. The computer program instructions may be stored in a storage device 1512 (e.g., magnetic disk) and loaded into memory 1510 when execution of the computer program instructions is desired. Thus, the steps of the methods of FIGS. 1, 2, 3, 4, 7, and 10 may be defined by the computer program instructions stored in the memory 1510 and/or storage 1512 and controlled by the processor 1504 executing the computer program instructions. An image acquisition device 1520, such as a CT scanning device, C-arm image acquisition device, MR scanning device, Ultrasound device, etc., can be connected to the computer 1502 to input image data to the computer 1502. It is possible to implement the image acquisition device 1520 and the computer 1502 as one device. It is also possible that the image acquisition device 1520 and the computer 1502 communicate wirelessly through a network. The computer 1502 also includes one or more network interfaces 1506 for communicating with other devices via a network. The computer 1502 also includes other input/output devices 1508 that enable user interaction with the computer 1502 (e.g., display, keyboard, mouse, speakers, buttons, etc.). Such input/output devices 1508 may be used in conjunction with a set of computer programs as an annotation tool to annotate volumes received from the image acquisition device 1520. One skilled in the art will recognize that an implementation of an actual computer could contain other components as well, and that FIG. 15 is a high level representation of some of the components of such a computer for illustrative purposes.

The foregoing Detailed Description is to be understood as being in every respect illustrative and exemplary, but not restrictive, and the scope of the invention disclosed herein is not to be determined from the Detailed Description, but rather from the claims as interpreted according to the full breadth permitted by the patent laws. It is to be understood that the embodiments shown and described herein are only illustrative of the principles of the present invention and that various modifications may be implemented by those skilled in the art without departing from the scope and spirit of the invention. Those skilled in the art could implement various other feature combinations without departing from the scope and spirit of the invention.

The invention claimed is:

1. A method for patient-specific planning and guidance of electrophysiological interventions, comprising:
generating a patient-specific anatomical heart model from cardiac image data of a patient;
generating a patient-specific cardiac electrophysiology model based on the patient-specific anatomical heart model and patient-specific electrophysiology measurements;
performing a virtual electrophysiological intervention using the patient-specific cardiac electrophysiology model; and
calculating an electrocardiogram (ECG) signal in response to the virtual electrophysiological intervention by:
calculating extra-cellular potentials based on trans-membrane potentials calculated using the patient-specific cardiac electrophysiology model at a plurality of points within the myocardium,
calculating body surface potentials at a plurality of points on the torso based on the extra-cellular potentials, and
calculating the ECG signal using the body surface potentials at points on the torso corresponding to ECG lead locations.

2. The method of claim 1, wherein generating a patient-specific anatomical heart model from cardiac image data of a patient comprises:
extracting a multi-component patient-specific heart morphology model from the cardiac image data;
fusing the multi-component patient-specific heart morphology model into a single heart model and tagging elements of the single heart model according to the multiple components; and
generating a model of myocardium fiber architecture based on the single heart model.

3. The method of claim 2, wherein generating a patient-specific anatomical heart model from cardiac image data of a patient further comprises:
segmenting at least one of scar or healing tissue in the cardiac image data; and
mapping the segmented at least one of scar or healing tissue to the single heart model.

4. The method of claim 2, wherein generating a patient-specific anatomical heart model from cardiac image data of a patient further comprises:
extracting a coronary sinus centerline from the cardiac image data; and
mapping the coronary sinus to the single heart model based on the extracted coronary sinus centerline.

5. The method of claim 1, further comprising:
registering the patient-specific electrophysiology measurements to the patient-specific anatomical heart model prior to generating the patient-specific cardiac electrophysiology model.

6. The method of claim 5, wherein the patient-specific electrophysiology measurements are pre-operative patient-specific electrophysiology measurements.

7. The method of claim 6, wherein the pre-operative patient-specific electrophysiology measurements include diagnostic endocardial mappings and registering the patient-specific electrophysiology measurements to the patient-specific anatomical heart model prior to generating the patient-specific cardiac electrophysiology model comprises:
registering the diagnostic endocardial mappings to the patient-specific anatomical heart model using spatial fiducials provided in the diagnostic endocardial mappings.

8. The method of claim 5, wherein the patient-specific electrophysiology measurements are intra-operative electrophysiology measurements acquired during an electrophysiology intervention.

9. The method of claim 8, wherein the intra-operative electrophysiology measurements include intra-operative endocardial mappings and registering the patient-specific electrophysiology measurements to the patient-specific anatomical heart model prior to generating the patient-specific cardiac electrophysiology model comprises one of:
    registering the intra-operative endocardial mappings to the patient-specific anatomical heart model using spatial fiducials provided in the intra-operative endocardial mappings; and
    registering the patient-specific anatomical heart model to medical image data acquired during the electrophysiological intervention.

10. The method of claim 1, wherein the patient-specific electrophysiology measurements include at least one of endocardial mappings, ECG measurements, or body surface mappings (BSM).

11. The method of claim 1, wherein generating a patient-specific cardiac electrophysiology model based on the patient-specific anatomical heart model and patient-specific electrophysiology measurements comprises:
    generating a Cartesian grid domain using the patient-specific anatomical heart model; and
    calculating transmembrane potential variation over time at each of a plurality of nodes within the myocardium in the Cartesian grid domain by computing a solution of a cardiac electrophysiology model for each of the plurality of nodes using a Lattice-Boltzmann method for electrophysiology.

12. The method of claim 11, wherein generating a patient-specific cardiac electrophysiology model based on the patient-specific anatomical heart model and patient-specific electrophysiology measurements further comprises:
    estimating parameters of the cardiac electrophysiology model using an inverse problem approach.

13. The method of claim 12, wherein estimating parameters of the cardiac electrophysiology model using an inverse problem approach comprises:
    calculating a cost function that compares cardiac electrophysiology calculated at the plurality of nodes using the cardiac electrophysiology model with the patient-specific electrophysiology measurements;
    estimating parameters of the cardiac electrophysiology model using an inverse problem algorithm to minimize the cost function; and
    re-calculating the transmembrane potential variation over time at each of the plurality of nodes within the myocardium in the Cartesian grid domain by computing a solution of a cardiac electrophysiology model with the estimated parameters for each of the plurality of nodes using the Lattice-Boltzmann method for electrophysiology.

14. The method of claim 1, wherein performing a virtual electrophysiological intervention using the patient-specific cardiac electrophysiology model comprises:
    calculating transmembrane potential variation over time at a plurality of points within the myocardium using the patient-specific cardiac electrophysiology model with a stimulus current added at a spatial location of a virtual pacing catheter.

15. The method of claim 14, wherein performing a virtual electrophysiological intervention using the patient-specific cardiac electrophysiology model further comprises:
    receiving a user input selecting the spatial location and pacing protocols of the virtual pacing catheter.

16. The method of claim 14, wherein performing a virtual electrophysiological intervention using the patient-specific cardiac electrophysiology model further comprises:
    automatically selecting a plurality of spatial locations and pacing protocols at which to perform virtual pacing.

17. The method of claim 16, wherein calculating transmembrane potential variation over time at a plurality of points within the myocardium using the patient-specific cardiac electrophysiology model with a stimulus current added at a spatial location of a virtual pacing catheter comprises:
    for each of the plurality of spatial locations, calculating the transmembrane potential variation over time at the plurality of points within the myocardium using the patient-specific cardiac electrophysiology model with a stimulus current added at that spatial location and applied at one or more different frequencies.

18. The method of claim 1, wherein performing a virtual electrophysiological intervention using the patient-specific cardiac electrophysiology model comprises:
    calculating transmembrane potential variation over time at a plurality of points within the myocardium using the patient-specific cardiac electrophysiology model with a stimulus current added at a spatial location of a virtual ablation catheter.

19. The method of claim 1, further comprising:
displaying a visualization of the ECG signal.

20. The method of claim 1, further comprising:
calculating one or more virtual ECG parameters based on the calculated ECG signal.

21. An apparatus for patient-specific planning and guidance of electrophysiological interventions, comprising:
    a processor; and
    a memory storing computer program instructions, which when executed by the processor cause the processor to perform operations comprising:
    generating a patient-specific anatomical heart model from cardiac image data of a patient;
    generating a patient-specific cardiac electrophysiology model based on the patient-specific anatomical heart model and patient-specific electrophysiology measurements;
    performing a virtual electrophysiological intervention using the patient-specific cardiac electrophysiology model; and
    calculating an electrocardiogram (ECG) signal in response to the virtual electrophysiological intervention by:
        calculating extra-cellular potentials based on transmembrane potentials calculated using the patient-specific cardiac electrophysiology model at a plurality of points within the myocardium,
        calculating body surface potentials at a plurality of points on the torso based on the extra-cellular potentials, and
        calculating the ECG signal using the body surface potentials at points on the torso corresponding to ECG lead locations.

22. The apparatus of claim 21, wherein generating a patient-specific anatomical heart model from cardiac image data of a patient comprises:
    extracting a multi-component patient-specific heart morphology model from the cardiac image data;
    fusing the multi-component patient-specific heart morphology model into a single heart model and tagging elements of the single heart model according to the multiple components; and
    generating a model of myocardium fiber architecture based on the single heart model.

23. The apparatus of claim 22, wherein generating a patient-specific anatomical heart model from cardiac image data of a patient further comprises:
  segmenting at least one of scar or healing tissue in the cardiac image data; and
  mapping the segmented at least one of scar or healing tissue to the single heart model.

24. The apparatus of claim 22, wherein generating a patient-specific anatomical heart model from cardiac image data of a patient further comprises:
  extracting a coronary sinus centerline from the cardiac image data; and
  mapping the coronary sinus to the single heart model based on the extracted coronary sinus centerline.

25. The apparatus of claim 21, wherein the operations further comprise:
  registering the patient-specific electrophysiology measurements to the patient-specific anatomical heart model prior to generating the patient-specific cardiac electrophysiology model.

26. The apparatus of claim 25, wherein the patient-specific electrophysiology measurements are pre-operative patient-specific electrophysiology measurements.

27. The apparatus of claim 25, wherein the patient-specific electrophysiology measurements are intra-operative electrophysiology measurements acquired during an electrophysiology intervention.

28. The apparatus of claim 21, wherein the patient-specific electrophysiology measurements include at least one of endocardial mappings, ECG measurements, or body surface mappings (BSM).

29. The apparatus of claim 21, wherein generating a patient-specific cardiac electrophysiology model based on the patient-specific anatomical heart model and patient-specific electrophysiology measurements comprises:
  generating a Cartesian grid domain using the patient-specific anatomical heart model; and
  calculating transmembrane potential variation over time at each of a plurality of nodes within the myocardium in the Cartesian grid domain by computing a solution of a cardiac electrophysiology model for each of the plurality of nodes using a Lattice-Boltzmann method for electrophysiology.

30. The apparatus of claim 29, wherein generating a patient-specific cardiac electrophysiology model based on the patient-specific anatomical heart model and patient-specific electrophysiology measurements further comprises:
  estimating parameters of the cardiac electrophysiology model using an inverse problem approach.

31. The apparatus of claim 30, wherein estimating parameters of the cardiac electrophysiology model using an inverse problem approach comprises:
  calculating a cost function that compares cardiac electrophysiology calculated at the plurality of nodes using the cardiac electrophysiology model with the patient-specific electrophysiology measurements;
  estimating parameters of the cardiac electrophysiology model using an inverse problem algorithm to minimize the cost function; and
  re-calculating the transmembrane potential variation over time at each of the plurality of nodes within the myocardium in the Cartesian grid domain by computing a solution of a cardiac electrophysiology model with the estimated parameters for each of the plurality of nodes using the Lattice-Boltzmann method for electrophysiology.

32. The apparatus of claim 21, wherein performing a virtual electrophysiological intervention using the patient-specific cardiac electrophysiology model comprises:
  calculating transmembrane potential variation over time at a plurality of points within the myocardium using the patient-specific cardiac electrophysiology model with a stimulus current added at a spatial location of a virtual pacing catheter.

33. The apparatus of claim 21, wherein performing a virtual electrophysiological intervention using the patient-specific cardiac electrophysiology model comprises:
  calculating transmembrane potential variation over time at a plurality of points within the myocardium using the patient-specific cardiac electrophysiology model with a stimulus current added at a spatial location of a virtual ablation catheter.

34. The apparatus of claim 21, wherein the operations further comprise:
  displaying a visualization of the ECG signal.

35. The apparatus of claim 21, wherein the operations further comprise:
  calculating one or more virtual ECG parameters based on the calculated ECG signal.

36. A non-transitory computer readable medium storing computer program instructions for patient-specific planning and guidance of electrophysiological interventions, the computer program instructions when executed by a processor cause the processor to perform operations comprising:
  generating a patient-specific anatomical heart model from cardiac image data of a patient;
  generating a patient-specific cardiac electrophysiology model based on the patient-specific anatomical heart model and patient-specific electrophysiology measurements;
  performing a virtual electrophysiological intervention using the patient-specific cardiac electrophysiology model; and
  calculating an electrocardiogram (ECG) signal in response to the virtual electrophysiological intervention by:
    calculating extra-cellular potentials based on transmembrane potentials calculated using the patient-specific cardiac electrophysiology model at a plurality of points within the myocardium,
    calculating body surface potentials at a plurality of points on the torso based on the extra-cellular potentials, and
    calculating the ECG signal using the body surface potentials at points on the torso corresponding to ECG lead locations.

37. The non-transitory computer readable medium of claim 36, wherein generating a patient-specific anatomical heart model from cardiac image data of a patient comprises:
  extracting a multi-component patient-specific heart morphology model from the cardiac image data;
  fusing the multi-component patient-specific heart morphology model into a single heart model and tagging elements of the single heart model according to the multiple components; and
  generating a model of myocardium fiber architecture based on the single heart model.

38. The non-transitory computer readable medium of claim 37, wherein generating a patient-specific anatomical heart model from cardiac image data of a patient further comprises:
  segmenting at least one of scar or healing tissue in the cardiac image data; and mapping the segmented at least one of scar or healing tissue to the single heart model.

39. The non-transitory computer readable medium of claim 37, wherein generating a patient-specific anatomical heart model from cardiac image data of a patient further comprises:
extracting a coronary sinus centerline from the cardiac image data; and
mapping the coronary sinus to the single heart model based on the extracted coronary sinus centerline.

40. The non-transitory computer readable medium of claim 36, wherein the operations further comprise:
registering the patient-specific electrophysiology measurements to the patient-specific anatomical heart model prior to generating the patient-specific cardiac electrophysiology model.

41. The non-transitory computer readable medium of claim 40, wherein the patient-specific electrophysiology measurements are pre-operative patient-specific electrophysiology measurements.

42. The non-transitory computer readable medium of claim 40, wherein the patient-specific electrophysiology measurements are intra-operative electrophysiology measurements acquired during an electrophysiology intervention.

43. The non-transitory computer readable medium of claim 36, wherein the patient-specific electrophysiology measurements include at least one of endocardial mappings, ECG measurements, or body surface mappings (BSM).

44. The non-transitory computer readable medium of claim 36, wherein generating a patient-specific cardiac electrophysiology model based on the patient-specific anatomical heart model and patient-specific electrophysiology measurements comprises:
generating a Cartesian grid domain using the patient-specific anatomical heart model; and
calculating transmembrane potential variation over time at each of a plurality of nodes within the myocardium in the Cartesian grid domain by computing a solution of a cardiac electrophysiology model for each of the plurality of nodes using a Lattice-Boltzmann method for electrophysiology.

45. The non-transitory computer readable medium of claim 44, wherein generating a patient-specific cardiac electrophysiology model based on the patient-specific anatomical heart model and patient-specific electrophysiology measurements further comprises:
estimating parameters of the cardiac electrophysiology model using an inverse problem approach.

46. The non-transitory computer readable medium of claim 45, wherein estimating parameters of the cardiac electrophysiology model using an inverse problem approach comprises:
calculating a cost function that compares cardiac electrophysiology calculated at the plurality of nodes using the cardiac electrophysiology model with the patient-specific electrophysiology measurements;
estimating parameters of the cardiac electrophysiology model using an inverse problem algorithm to minimize the cost function; and
re-calculating the transmembrane potential variation over time at each of the plurality of nodes within the myocardium in the Cartesian grid domain by computing a solution of a cardiac electrophysiology model with the estimated parameters for each of the plurality of nodes using the Lattice-Boltzmann method for electrophysiology.

47. The non-transitory computer readable medium of claim 36, wherein performing a virtual electrophysiological intervention using the patient-specific cardiac electrophysiology model comprises:
calculating transmembrane potential variation over time at a plurality of points within the myocardium using the patient-specific cardiac electrophysiology model with a stimulus current added at a spatial location of a virtual pacing catheter.

48. The non-transitory computer readable medium of claim 36, wherein performing a virtual electrophysiological intervention using the patient-specific cardiac electrophysiology model comprises:
calculating transmembrane potential variation over time at a plurality of points within the myocardium using the patient-specific cardiac electrophysiology model with a stimulus current added at a spatial location of a virtual ablation catheter.

49. The non-transitory computer readable medium of claim 36, wherein the operations further comprise:
displaying a visualization of the ECG signal.

50. The non-transitory computer readable medium of claim 36, wherein the operations further comprise:
calculating one or more virtual ECG parameters based on the simulated ECG signal.

* * * * *